(12) United States Patent
Zeltinger et al.

(10) Patent No.: US 7,473,417 B2
(45) Date of Patent: Jan. 6, 2009

(54) INHERENTLY RADIOPAQUE BIORESORBABLE POLYMERS FOR MULTIPLE USES

(75) Inventors: Joan Zeltinger, Encinitas, CA (US); Donald K. Brandom, Davis, CA (US)

(73) Assignee: REVA Medical, Inc., San Diego, CA (US)

( * ) Notice: Subject to any disclaimer, the term of this patent is extended or adjusted under 35 U.S.C. 154(b) by 275 days.

(21) Appl. No.: 11/200,656

(22) Filed: Aug. 10, 2005

(65) Prior Publication Data

US 2006/0036316 A1 Feb. 16, 2006

Related U.S. Application Data

(60) Provisional application No. 60/601,526, filed on Aug. 13, 2004.

(51) Int. Cl.
*A61K 31/74* (2006.01)
*A61F 2/06* (2006.01)

(52) U.S. Cl. .................... 424/78.08; 623/1.34
(58) Field of Classification Search ............... 623/1.42, 623/1.43, 1.46, 1.1, 1.3, 1.34; 424/9.451, 424/78.08; 604/103.1; 523/117
See application file for complete search history.

(56) References Cited

U.S. PATENT DOCUMENTS

| | | | |
|---|---|---|---|
| 4,638,045 A | 1/1987 | Kohn et al. | |
| 4,863,735 A | 9/1989 | Kohn et al. | |
| 4,980,449 A | 12/1990 | Kohn et al. | |
| 5,198,507 A | 3/1993 | Kohn et al. | |
| 5,443,477 A * | 8/1995 | Marin et al. | 606/198 |
| 5,466,439 A * | 11/1995 | Gibby et al. | 424/9.365 |
| 5,469,867 A | 11/1995 | Schmitt | |
| 5,670,602 A | 9/1997 | Kohn et al. | |
| 5,912,225 A | 6/1999 | Mao et al. | |
| 6,015,424 A | 1/2000 | Rosenbluth et al. | |
| 6,200,338 B1 * | 3/2001 | Solomon et al. | 623/1.34 |
| 6,238,687 B1 | 5/2001 | Mao et al. | |
| 6,375,669 B1 | 4/2002 | Rosenbluth et al. | |
| 6,388,043 B1 | 5/2002 | Langer et al. | |
| 6,475,477 B1 | 11/2002 | Kohn et al. | |
| 6,492,462 B2 | 12/2002 | Bitler et al. | |
| 6,544,453 B2 | 4/2003 | Taft et al. | |

(Continued)

FOREIGN PATENT DOCUMENTS

WO WO 98/46286 10/1998

(Continued)

OTHER PUBLICATIONS

Jayakrishnan et al., "Synthesis and Polymerization of Some Iodine-Containing Monomers for Biomedical Applications", Journal of Applied Polymer Science, Vo. 44, 743-748 (1992).

(Continued)

*Primary Examiner*—Thomas J Sweet
*Assistant Examiner*—Jonathan R Stroud
(74) *Attorney, Agent, or Firm*—Knobbe Martens Olson & Bear LLP

(57) ABSTRACT

Preferred embodiments of the present invention relate to polymeric medical devices, such as stents. More particularly, the compositions disclosed herein comprise halogen-containing phenol moieties, that may be used for medical devices and other uses whereby bioresorbable and radiopaque and physicomechanical properties are desired.

30 Claims, 1 Drawing Sheet

U.S. PATENT DOCUMENTS

| | | | |
|---|---|---|---|
| 6,550,480 | B2 | 4/2003 | Feldman et al. |
| 6,599,448 | B1 * | 7/2003 | Ehrhard et al. ............... 252/582 |
| 6,623,521 | B2 * | 9/2003 | Steinke et al. ............... 623/1.16 |
| 6,652,572 | B2 * | 11/2003 | Kugler et al. ............... 623/1.13 |
| 6,831,116 | B2 | 12/2004 | Bitler et al. |
| 6,932,930 | B2 | 8/2005 | DeSimone et al. |
| 2001/0046505 | A1 | 11/2001 | Kohn et al. |
| 2004/0086461 | A1 | 5/2004 | Kohn et al. |
| 2004/0127970 | A1 * | 7/2004 | Saunders et al. ........... 623/1.15 |
| 2005/0106119 | A1 | 5/2005 | Brandom |

FOREIGN PATENT DOCUMENTS

| | | |
|---|---|---|
| WO | WO 99/24391 A | 5/1999 |
| WO | WO 2006/014596 | 2/2006 |
| WO | WO 2006/020616 | 2/2006 |

OTHER PUBLICATIONS

Kruft et al., "*In vivo* tissue compatibility of two radio-opaque polymeric biomaterials", Biomaterials Vo. 18 No. 1 31-36 (1997).

Kruft et al., "Studies on radio-opaque polymeric biomaterials with potential applications to endovascular prostheses", Biomaterials Vo. 17 No. 18, 1803-1812 (1996).

Mao, et al., "Synthesis and Biological Properties of Polymer Immunoadjuvants", Polymer Journal, vol. 25, No. 5, pp. 499-505 (1993).

Cabasso et al., "Radiopaque Polymers Based on Acrylated Phosphonate Esters Derived from Polyols", Journal of Applied Polymer Science, vol. 41, 3025-3042 (1990).

Cabasso et al., " Radiopasque Miscible Systems Composed of Poly (Methyl Methacrylate) and Transition and Nontransition Metal Salts: Spectroscopic, Thermal, and Radiographic Characterization", Journal of Applied Polymer Science, Vo. 38, 1653-1666 (1989).

U.S. Appl. No. 11/176,638 filed on Jul. 7, 2005.

PCT Search Report for PCT/US2005/028228.

Aharoni, et al., "Rigid Backbone Polymers. 2. Polyisocyanates and Their Liquid-Crystal Behavior" *Macromolecules*, 12(1):94-103 (1979).

Andruzzi, et al., "Studies on Comb-like Polymers. 2. Poly(octadecylethylene oxide)" *Macromolecules*, 13:15-18(1980).

Chupov, et al., "Structure and Physico-Chemical Properties of Comb-Like Polypeptides Based on Poly-L-Lysine*" *Polymer Science U.S.S.R.* 21:241-252 (1979).

Gonzalez, et al. Side-Chain Crystallinity, Heat of Melting, and Thermal Transitions in poly[N- (10-n-Alkyloxycarbonyl-n-Decyl)Maleimides] (PEMI) *Journal of Polymer Science: Polymer Physics Edition*. 18:2197-2207 (1980).

Greenberg, et al., "Side Chain Crystallization of n-Alkyl Polymethacrylates and Polyacrylates" *Institute of Polymer Research, Polytechnic Institute of Brooklyn*. 76:6280-6285. (1954).

Hooper, et al., "Diphenolic monomers derived form the natural amino acid alpha-l-tyrosine: an evaluation of peptide coupling techniques" *Journal of Bioactive and Compatible Polymers*, 10(4):327-340 XP002045571.

Jordan, et al., "Side-Chain Crystallinity. I. Heats of Fusion and Melting Transitions on Selected Homopolymers Having Long Side Chains" *Journal of Polymer Science: Part A-1*, 9:1835-1852 (1971).

Jordan, et al., "Side-Chain Crystallinity. II. Heats of Fusion and Melting Transitions on Selected Copolymers Incorporating n-Octadecyl Acrylate of Vinyl Stearate" *Journal of Polymer Science:Part A-1*, 9:3349-3365 (1971).

Jordan, et al., "Side-Chain Crystallinity. III. Influence of Side-Chain Crystallinity on the Glass Transition Temperatures of Selected Copolymers Incorporating n-Octadeeyl Acrylate or Vinyl Stearate" *Journal of Polymer Science: Part A-1* 9:3367-3378(1971).

Jordan, et al., "Side-Chain Crystallinity. V. Heats of Fusion and Melting Temperatures on Monomers Whose Homopolymers Have Long Side Chains" *Journal of Polymer Science*, 10:3347-3366 (1972).

Magagnini, et al., "Studies on Comb-like Polymers. 1. Poly(octadecylethylene)" *Macromolecules*, 13:12-15(1980).

O'Driscoll, et al., "Kinetics of Anionic Copolymerization of Monomers of Similar Polarities" *Journal of Polymer Science*, 61:19-24 (1962).

Overberger, et al., "The Preparation and Polymerization of *p*-Alkylstyrenes. Effect of Structure on the TransitionTemperatures of the Polymers" *The Department of Chemistry, Institute of Polymer Research, Polytechnic Institute of Brooklyn*. 75:3326-3330.

Pittman, et al., "Effect of Polymer Crystallinity on the Wetting Properties of Certain Fluroalkyl Acrylates" *Journal of Polymer Science Part A-1*, 7:3053-3066 (1969).

Plate, et al., "Comb-Like Polymers. Structure and Properties" *J. Polymer Sci.:Macromolecular Reviews*, 8:117-253(1974).

Pulapura, et al., "Structure-Property Relationships for the Design of Polyiminocarbonates" *Biomaterials* 11(9):666-678. XP000172545.

Rabolt, et al., "Studies of Chain Conformational Kinetics in Poly(di-*n*-alkylsilanes) by Spectroscopic Methods. 1.Poly(di-*n*-hexylsilane), Poly(di-*n*-heptylsaline), and Poly(di-*n*-octylsilane)." *Macromolecules*, 19:611-616 (1986).

Wada, et al., "Effect of Amount of Medium on the Radiation-Induced Polymerization of Ethylene *in tert*-Butyl Alcohol" *Journal of Polymer Science: Part A-1*, 10:1655-1667 (1972).

Watanabe, et al., "Thermotropic Polypeptides. 2. Molecular Packing and Thermotropic Behavior of Poly (L-glutamates) with Long *n*-Alkyl Side Chains", *Macromolecules* 18:2141-2148 (1985).

International Search Report for Application No. PCT/US2005/024289 mailed Dec. 6, 2005.

U.S. Appl. No. 11/335,771 filed on Jan. 18, 2006.

Hutmacher et al., Scaffold-based tissue engineering: rationale for computer-aided design and solid free-form fabrication systems. Trends in Biotechnology, vol. 22 No. 7, Jul. 2004, pp. 354-362.

The International Search Report and the Written Opinion of the International Searching Authority in the PCT/US2007/081566. Mailing date: Aug. 28, 2008.

* cited by examiner

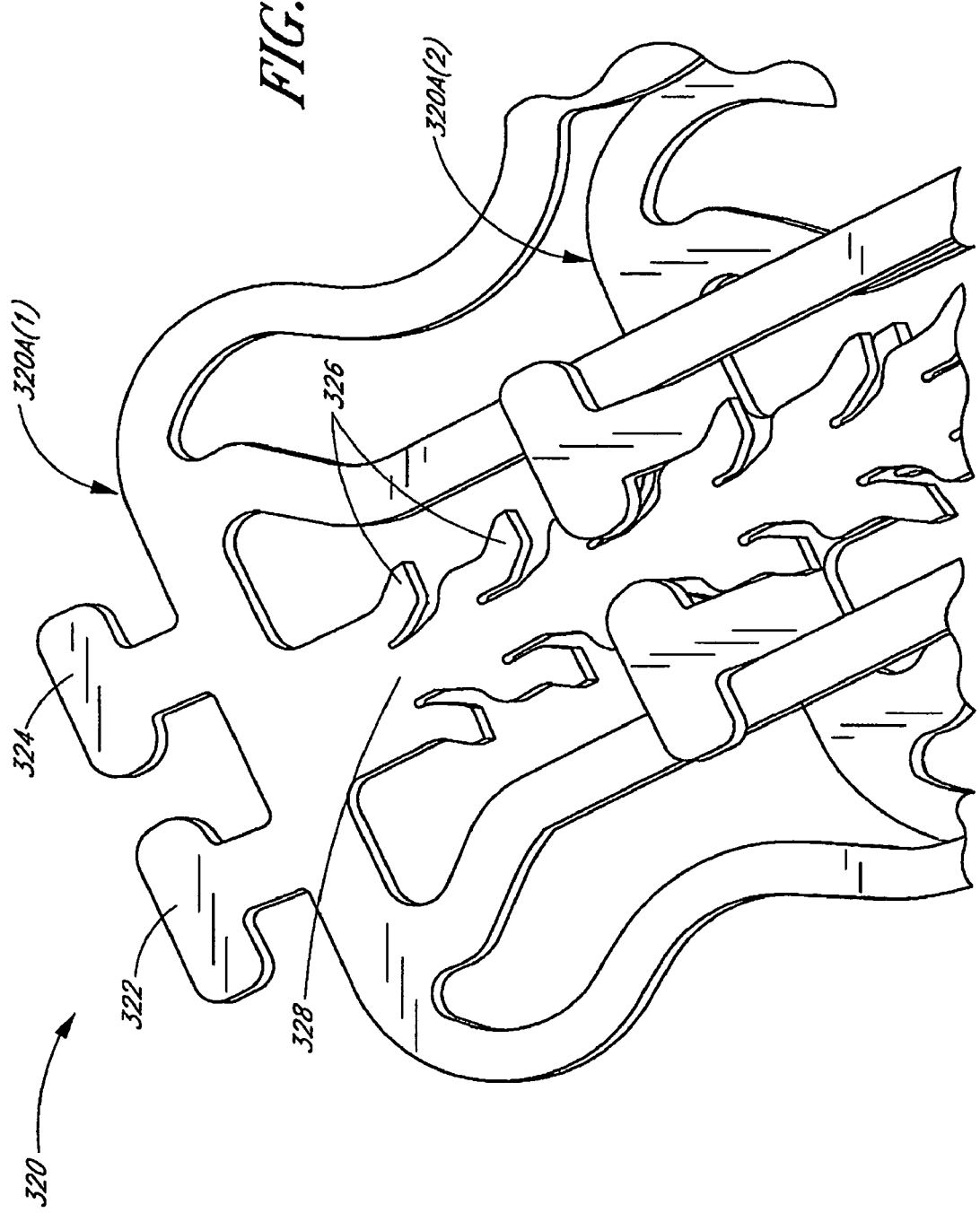

US 7,473,417 B2

INHERENTLY RADIOPAQUE BIORESORBABLE POLYMERS FOR MULTIPLE USES

CROSS-REFERENCE TO RELATED APPLICATIONS

This application claims benefit under 35 U.S.C. § 119(e) of U.S. Provisional Patent Application No. 60/601,526, filed Aug. 13, 2004.

BACKGROUND OF THE INVENTION

1. Field of the Invention

Preferred embodiments of the present invention relate to inherently radiopaque bioresorbable polymers for use in fabricating medical devices, such as stents. More particularly, the polymeric compositions comprise halogen-containing phenol moieties.

2. Description of the Related Art

Medical devices comprised of metal or polymer are used for numerous clinical applications every day. Metal medical devices are generally radiopaque due to the nature of the material whereas polymer medical devices are generally not naturally radiopaque. Hence, there remains a need for additional radiopaque bioresorbable polymeric formulations for use in devices that provide the advantage of radiopacity for a variety of medical procedures. A prime example of such a device includes vascular stents which are described below.

Vascular stents are used widely in a variety of applications, including, especially, in the treatment of heart disease. It has been reported that in 1998, about 61 million Americans had some form of heart disease, which since about 1990 has been the single leading cause of death in the United States. One type of heart disease, coronary artery disease (CAD), is characterized, at least in part, by the inhibition of blood flow through the arteries that supply blood to the heart muscle due to the buildup of plaque (arteriosclerosis) in the arteries. CAD is suspected to account for 1 out of every 5 deaths that occur in the U.S.A. In 2001, about 1.1 million people had a new or recurrent myocardial infarction (heart attack due to coronary arterial disease). See, for example, Report by the American Heart Association, "Heart and Stroke Statistical Update", 2001, American Heart Association, Dallas, Tex. Currently more than 500,000 Americans are treated annually for blocked coronary arteries. This number is expected to double over the next 10 years in light of the aging population.

Vascular stents generally comprise a mesh tube, which is inserted into an artery to keep the artery open after it has been stretched with a balloon during the course of an angioplasty procedure. Typically, the vascular stent is mounted on a balloon catheter that is inserted via the femoral artery and pushed to the desired location in the coronary artery. There, the balloon is inflated, thus expanding the stent and pressing it against the vessel wall to lock it in place.

Most stents are constructed from metal, including, for example, stainless steel or nitinol. While such metal stents possess certain desirable characteristics, such as sufficient radial strength to hold open a subject artery and radio-opacity (allowing an implanted stent to be seen and monitored by X-ray radiography/fluoroscopy), metal stents also exhibit a number of significant disadvantages. For example, the insertion and expansion of a metal stent in an artery tends to further injure the diseased vessel, potentially leading to the development of intimal hyperplasia and further occlusion of the vessel by the resulting in-growth of smooth muscle cells and matrix proteins through the stent struts. Another disadvantage associated with use of metal stents is that once deployed, they become permanent residents within the vessel walls—long after their usefulness has passed. Indeed, the useful lifespan of a stent is estimated to be in the range of about 6 to 9 months. After this time, the chronic stresses and strains imposed on the vessel architecture by the permanent metal implants are believed to promote in-stent restenosis. Another disadvantage associated with the use of metal stents is that the placement of multiple permanent metal stents within a vessel may be a barrier to subsequent surgical bypass. Further, the deployment of a first metal stent may become a physical hurdle to the later delivery of a second stent at a distal site within the same vessel. In contrast to a metal stent, a bioresorbable stent may not outlive its usefulness within the vessel. Moreover, a bioresorbable stent may be used to deliver a greater dose of a therapeutic, as a drug and/or biological agent could be coated on the stent as well as embedded in the device itself. Further, such a stent could deliver multiple drugs and/or biological agents, at the same time or at various times of its life cycle, to treat specific aspects or events of vascular disease. Additionally, a bioresorbable stent may also allow for repeat treatment of the same approximate region of the blood vessel.

U.S. Pat. No. 6,475,477 ("the '477 patent") teaches medical devices formed from radiopaque biocompatible polymers with hydrolytically unstable polymer backbones and pendant free carboxylic acid groups that promote polymer degradation and resorption; incorporated herein in its entirety by reference. Not only are many of the disclosed polymers less than ideal for use in stents, the polymers with free carboxylic acid groups are prepared from monomers with benzyl-protected free acid moieties that are selectively removed from the polymer via hydrogenolysis in the presence of a palladium catalyst and hydrogen. While such a method is effective for removing the benzyl protecting groups with little or no cleaving of the polymer backbone, the palladium catalyst used therein is relatively expensive, and traces of palladium are difficult to remove from the polymer product.

Some of the aforementioned deficiencies of the '477 patent have been addressed in U.S. patent application Ser. No. 11/176,638, filed Jul. 7, 2005, and Ser. No. 10/952,274, filed Sep. 27, 2004, both of which are incorporated herein by reference in their entireties. However, there remains a need for additional radiopaque bioresorbable polymeric formulations that provide advantageous physicochemical properties adapted for use in fabricating a variety of implantable medical devices.

Reference: Hutmacher D W, Sittinger M, Risbud M V. Scaffold-based tissue engineering: rationale for computer-aided design and solid free-form fabrication systems. Trends Biotechnol. 2004 July; 22(7):354-62.

SUMMARY OF THE INVENTION

For purposes of summarizing the invention, certain aspects, advantages and novel features of the invention have been described herein above. Of course, it is to be understood that not necessarily all such advantages may be achieved in accordance with any particular embodiment of the invention. Thus, the invention may be embodied or carried out in a manner that achieves or optimizes one advantage or group of advantages as taught or suggested herein without necessarily achieving other advantages as may be taught or suggested herein.

An embodiment provides an inherently radiopaque, biocompatible, bioresorbable polymer, wherein the polymer comprises one or more recurring units of the Formula (I):

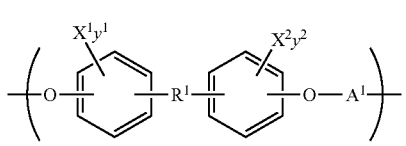
(I)

wherein:

$X^1$ and $X^2$ are each independently selected from the group consisting of Br and I;

y1 and y2 are each independently zero or an integer in the range of 1 to 4, with the proviso that the sum of y1 and y2 is at least one;

$R^1$ is

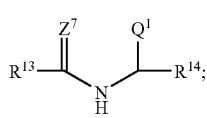

$R^{13}$ and $R^{14}$ are each independently selected from the group consisting of —CH=CH—, —$(CH_2)_c$—, —$(CHJ^1)_c$—, —$CHJ^2$—$CHJ^3$—, —CH=CH—$(CHJ^1)$—, and —$(CH_2)_c$—$(CHJ^1)$—;

c is zero or an integer in the range of 1 to 8;

$J^1$, $J^2$ and $J^3$ are each independently selected from the group consisting of H, Br, I, —NH-$Q^2$ and —C(=$Z^8$)-$OQ^3$;

$Q^1$, $Q^2$ and $Q^3$ are each independently H or a non-crystallizable group comprising from about 1 to about 30 carbons;

$Z^7$ and $Z^8$ are each independetly O or S;

$A^1$ is selected from the group consisting of

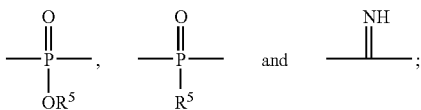

$R^5$ is selected from the group consisting of H, $C_1$-$C_{30}$ alkyl, and $C_1$-$C_{30}$ heteroalkyl. In a preferred embodiment, $X^1$, $X^2$, y1 and y2 are selected so that $X^1$ and $X^2$ are present in an amount that is effective to render the polymer radiopaque.

In an embodiment of a polymer comprising a recurring unit of the Formula (I), $R^1$ in Formula (I) is:

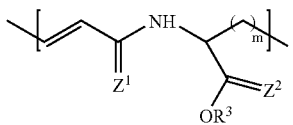

wherein $R^3$ is H or a non-crystallizable $C_1$ to $C_{29}$ hydrocarbon;

$Z^1$ and $Z^2$ are each independently O or S; and m is an integer in the range of 1 to 8.

In another embodiment of a polymer comprising a recurring unit of the Formula (I), $R^1$ in Formula (I) is:

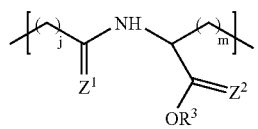

wherein $R^3$ is H or a non-crystallizable $C_1$ to $C_{29}$ hydrocarbon;

$Z^1$ and $Z^2$ are each independently O or S; and j and m are each independently an integer in the range of 1 to 8.

In another embodiment of a polymer comprising a recurring unit of the Formula (I), $R^1$ in Formula (I) is:

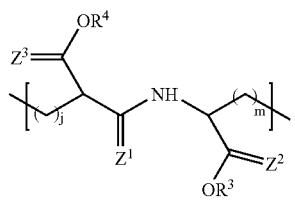

wherein $R^3$ and $R^4$ are each independently H or a non-crystallizable $C_1$ to $C_{29}$ hydrocarbon;

$Z^1$, $Z^2$ and $Z^3$ are each independently O or S; and j and m are each independently an integer in the range of 1 to 8.

Another embodiment provides a medical device that comprises an inherently radiopaque, biocompatible, bioresorbable polymer, wherein the polymer comprises one or more recurring units of the Formula (I) as described above. In a preferred embodiment, the medical device comprises a stent. Another embodiment provides a system for treating a site within a vessel, comprising such a stent and a catheter having a deployment means, wherein said catheter is adapted to deliver the stent to said site and said deployment means is adapted to deploy the stent. Another embodiment provides a method for re-treatment of a body lumen, comprising deploying such a stent along a region within a blood vessel, wherein such a stent resides for a period of time; and deploying at a later time a second stent, along the approximate same region within the blood vessel, such that the blood vessel is re-treated.

Another embodiment provides an inherently radiopaque, biocompatible, bioresorbable polymer, wherein the polymer comprises one or more recurring units of the Formula (I) as defined above, and further comprises one or more recurring units of the Formula (II):

(II)

wherein:

B is —O—$(CHR^6)_p$—$O)_q$—;

$R^6$ is H or $C_1$ to $C_3$ alkyl;

p and q are each individually an integer in the range of about 1 to about 100;

$A^2$ is selected from the group consisting of

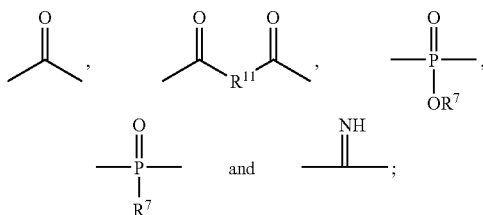

wherein $R^7$ is H or a $C_1$ to $C_{30}$ hydrocarbon and $R^{11}$ is selected from the group consisting of $C_1$-$C_{30}$ alkyl, $C_1$-$C_{30}$ heteroalkyl, $C_5$-$C_{30}$ aryl, $C_6$-$C_{30}$ alkylaryl, and $C_2$-$C_{30}$ heteroaryl. Another embodiment provides a medical device that comprises such a polymer. In an embodiment, B is an aliphatic linear or branched diol or a poly(alkylene glycol) unit.

Another embodiment provides an inherently radiopaque, biocompatible, bioresorbable polymer, wherein the polymer comprises one or more recurring units of the Formula (I) and one or more recurring units of the Formula (II), each as defined above, and further comprises one or more recurring units of the Formula (Ia):

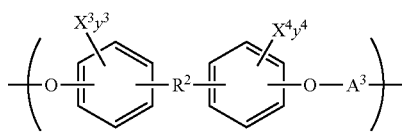

wherein:

$X^3$ and $X^4$ are each independently selected from the group consisting of Br and I;

y3 and y4 are each independently zero or an integer in the range of 1 to 4;

$R^2$ is selected from the group consisting of

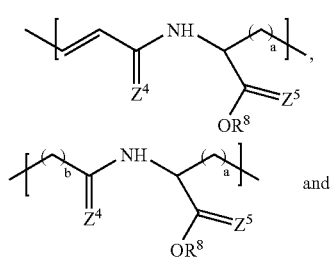

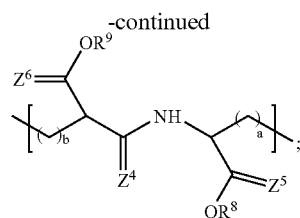

$R^8$ and $R^9$ are each independently H or a non-crystallizable $C_1$ to $C_{30}$ hydrocarbon;

$Z^4$, $Z^5$ and $Z^6$ are each independently O or S;

a and b are each independently an integer in the range of 1 to 8;

$A^3$ is selected from the group consisting of

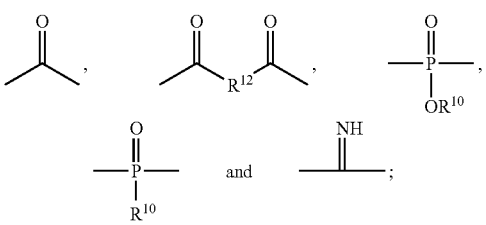

wherein $R^{10}$ is selected from the group consisting of H, $C_1$-$C_{30}$ alkyl, and $C_1$-$C_{30}$ heteroalkyl; and wherein $R^{12}$ is selected from the group consisting of $C_1$-$C_{30}$ alkyl, $C_1$-$C_{30}$ heteroalkyl, $C_5$-$C_{30}$ aryl, $C_6$-$C_{30}$ alkylaryl, and $C_2$-$C_{30}$ heteroaryl. Another embodiment provides a medical device that comprises such a polymer.

In certain embodiments, the polymer may comprise one or more recurring units of the formulae (I), (Ia), and/or (II). For example, another embodiment provides an inherently radiopaque, biocompatible, bioresorbable polymer, wherein the polymer comprises one or more recurring units of the Formula (III):

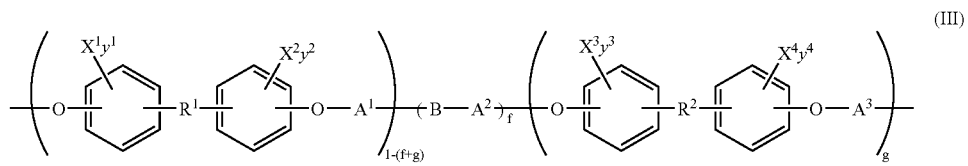

wherein $X^1$, $X^2$, $X^3$, $X^4$, y1, y2, y3, y4, $R^1$, $R^2$, $A^1$, $A^2$, $A^3$ and B are as defined above, and wherein f and g may each independently range from 0 to 1, e.g., as compositional/performance requirements dictate, with the proviso that the sum of f and g is less than 1. Another embodiment provides a medical device that comprises such a polymer.

In preferred embodiments of the medical devices summarized above, the device is a stent. In variations, the stent further comprises a configuration selected from the group consisting of a sheet stent, a braided stent, a self-expanding stent, a wire stent, a deformable stent, and a slide-and-lock stent. In another variation, the stent comprises at least two substantially non-deforming elements arranged to form a tubular member, the non-deforming elements being slidably and/or rotatably interconnected for allowing the tubular member to expand from a collapsed diameter to an expanded diameter.

In another variation to the stent, it further comprises a tubular member comprising a series of slideably-engaged radial elements and a locking mechanism adapted to permit one-way sliding of the radial elements, such that said tubular member is configured to expand from a first collapsed diameter to a second expanded diameter with minimum recoil.

In preferred embodiments of the medical device, the $X^1$ and $X^2$ groups on the polymer are iodine.

In a preferred embodiment, the medical device further comprises an effective amount of a therapeutic agent. Preferably, the amount is sufficient to inhibit restenosis, thrombosis, plaque formation, plaque rupture, and inflammation, lower cholesterol, and/or promote healing.

In another variation to the medical device, the polymer forms a coating on at least a portion of the medical device.

Another embodiment provides a system for treating a site within a vessel. The system comprises a catheter having a deployment means, and a stent as summarized above, comprising a radiopaque, biocompatible, bioresorbable polymer, wherein the catheter is adapted to deliver the stent to the site and the deployment means is adapted to deploy the stent. In some preferred embodiments, the catheter is selected from the group consisting of over-the-wire catheters, coaxial rapid-exchange catheters, and multi-exchange delivery catheters.

Another embodiment provides a method for re-treatment of a body lumen. The method comprises the steps of: deploying a first stent along a region within a blood vessel, wherein the first stent comprises the above-described radiopaque, biocompatible, bioresorbable polymer, and wherein the first stent resides for a period of time; and deploying at a later time a second stent, bioresorbable or metal or other, along the approximate same region within the blood vessel, such that the blood vessel is re-treated.

In other aspects of the invention, the polymer comprises a backbone which is not naturally occurring. Alternatively and/or additionally, the polymer may comprise a backbone comprising at least one amino acid derivative.

In preferred embodiments, the medical device is configured for placement in a region of the vascular, musculoskeletal/orthopedic, nervous, respiratory, reproductive, urinary, digestive, endocrine, hematopoietic and/or the integumentary system. In an embodiment, the medical device is configured for placement in the reprductive system for use other than the treatment of uterine fibroids.

In another embodiment, the medical device comprises a non-halogenated coating.

The foregoing and other objects, features and advantages of the present invention are more readily apparent from the detailed description of the preferred embodiments set forth below.

BRIEF DESCRIPTION OF THE DRAWING

FIG. 1 is a detailed view of a slide-and-lock stent configuration in accordance with one preferred embodiment of the present invention, comprising deflectable teeth which deflect downward to provide a stent exhibiting mono-directional expansion.

DETAILED DESCRIPTION OF THE PREFERRED EMBODIMENTS

In order to meet the important needs with respect to development of bioresorbable, radiopaque stents, the inventors have developed certain polymeric materials that comprise a recurring unit of the Formula (I). Preferred polymers comprising a recurring unit of the Formula (I) contain combinations of derivatives of structural units selected from dicarboxylic acids, halogenated (e.g., iodinated or brominated) derivatives of desaminotyrosyl-tyrosine and poly(alkylene glycols), which exhibit desirable physicomechanical and physicochemical properties that are consistent with their use in fabrication of medical devices, including stents. For example, the stents described in accordance with preferred embodiments of the present invention: (a) are sufficiently radiopaque to be visible by conventional X-ray fluoroscopy; (b) are of sufficient strength to support medically relevant levels of radial compression within an artery or surrounding tissue; and/or (c) have a desirable resorption profile that may be adjusted to account for the needs of a range of applications requiring the presence of a stent for different lengths of time or for the elution of therapeutics.

Although the inventors do not wish to be bound by or to any particular theory of operation, the inventors believe that the beneficial combination of properties associated with the medical devices of the present invention are attributable, at least in part, to certain characteristics of the polymers of Formula (I), from which the devices are made.

It is understood that the polymers described herein may be used in accordance with preferred aspects of the invention as a homogeneous polymer, as a copolymer, and/or as a polymer blend. Accordingly, reference herein to a polymer of the Formula (I) is understood to be a reference to a polymer that comprises a recurring unit of the Formula (I), which may be a homopolymer, copolymer or blend.

The bioresorbable, inherently radiopaque stents disclosed in accordance with preferred embodiments of the present invention may be used, for example, to temporarily treat a blood vessel as in traditional applications which generally include delivery through a catheter.

Applicants have discovered that a biocompatible, bioresorbable, inherently radiopaque polymer class may be produced from a broad class of aryl-containing biocompatible, bioresorbable polymers. For example, in all of the biocompatible, bioresorbable polymers noted in the table below, radiopacity may be introduced to the aromatic rings via halogenation, particularly bromination and iodination, by well-known techniques that may be readily employed by those of ordinary skill in the art without undue experimentation, in light of the disclosure provided herein. U.S. Pat. No. 6,475,477 reveals a broad class of inherently radiopaque, biocompatible, bioresorbable polymers made in this manner. Radiopacity may be imparted to the other polymers in Table 1 in a like fashion, e.g., by halogenation of the monomers from which the polymers are made and/or by halogenation of the polymer itself. The entire disclosures of each of the patents listed in TABLE 1 are incorporated herein by reference, and particularly for the purposes of describing the manner in which the various polymers are made.

TABLE 1

| U.S. Pat. No. | Patent Title | What is taught |
| --- | --- | --- |
| 4,863,735 | Biodegradable polymeric drug delivery system with adjuvant activity | Poly(iminocarbonate) syntheses |
| 4,980,449 | Polyiminocarbonate synthesis | Polyiminocarbonate syntheses |
| 6,238,687 | Biodegradable polymers, compositions, articles and methods for making and using the same | Processes for preparing phosphorus and desaminotyrosyl L-tyrosine linkages in the polymer backbone |
| 5,912,225 | Biodegradable poly (phosphoester-co-desaminotyrosyl L-tyrosine ester) compounds, compositions, articles and methods for making and using the same | Processes for preparing polymers containing phosphorus and desaminotyrosyl L-tyrosine linkages |
| 4,638,045 | Non-peptide polyamino acid bioerodible polymers | Polymers with a plurality of monomer units of two or three amino acids |

For example, an embodiment provides an inherently radiopaque, biocompatible, bioresorbable polymer, wherein the polymer comprises one or more recurring units of the Formula (I):

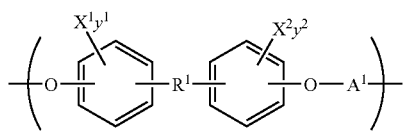

(I)

wherein:

$X^1$ and $X^2$ are each independently selected from the group consisting of Br and I;

y1 and y2 are each independently zero or an integer in the range of 1 to 4, with the proviso that the sum of y1 and y2 is at least 1;

$R^1$ is

$R^{13}$ and $R^{14}$ are each independently selected from the group consisting of —CH=CH—, —(CH$_2$)$_c$—, —(CHJ$^1$)—, —CHJ$^2$—CHJ$^3$—, —CH=CH—(CHJ$^1$)—, and —(CH$_2$)$_c$—(CHJ$^1$)—;

c is zero or an integer in the range of 1 to 8;

$J^1$, $J^2$ and $J^3$ are each independently selected from the group consisting of H, Br, I, —NH-Q$^2$ and —C(=Z$^8$)—OQ$^3$;

$Q^1$, $Q^2$ and $Q^3$ are each independently H or a non-crystallizable group comprising from about 1 to about 30 carbons;

$Z^7$ and $Z^8$ are each independetly O or S;

$A^1$ is selected from the group consisting of

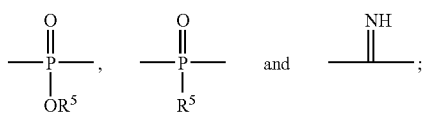

$R^5$ is selected from the group consisting of H, $C_1$-$C_{30}$ alkyl, and $C_1$-$C_{30}$ heteroalkyl. In a preferred embodiment, $X^1$, $X^2$, y1 and y2 are selected so that $X^1$ and $X^2$ are present in an amount that is effective to render the polymer radiopaque.

In various embodiments, $R^1$ is selected from the group consisting of

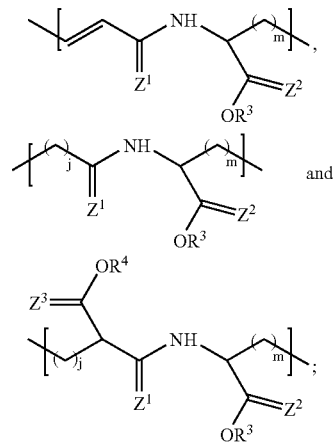

wherein $R^3$ and $R^4$ are each independently H or a non-crystallizable $C_1$ to $C_{30}$ hydrocarbon;

$Z^1$, $Z^2$ and $Z^3$ are each independently O or S; and j and m are each independently an integer in the range of 1 to 8.

Another embodiment provides an inherently radiopaque, biocompatible, bioresorbable polymer, wherein the polymer comprises one or more recurring units of the Formula (I) as defined above, and further comprises one or more recurring units of the Formula (II):

$$-\!\!\left(\!\text{B}-\text{A}^2\!\right)\!\!-$$

(II)

wherein:

B is —O—(CHR$^6$)$_p$—O)$_q$—;

$R^6$ is H or $C_1$ to $C_3$ alkyl;

p and q are each individually an integer in the range of about 1 to about 100;

$A^2$ is selected from the group consisting of

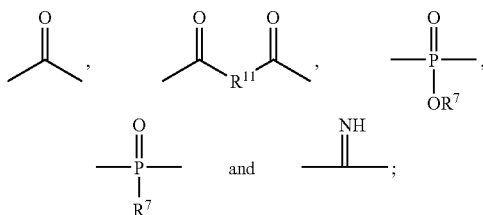

wherein $R^7$ is H or a $C_1$ to $C_{30}$ hydrocarbon and $R^{11}$ is selected from the group consisting of $C_1$-$C_{30}$ alkyl, $C_1$-$C_{30}$ heteroalkyl, $C_5$-$C_{30}$ aryl, $C_6$-$C_{30}$ alkylaryl, and $C_2$-$C_{30}$ heteroaryl. Another embodiment provides a medical device that comprises such a polymer. In an embodiment, B is an aliphatic linear or branched diol or a poly(alkylene glycol) unit.

Another embodiment provides an inherently radiopaque, biocompatible, bioresorbable polymer, wherein the polymer comprises one or more recurring units of the Formula (I) and/or one or more recurring units of the Formula (II), each as defined above, and/or further comprises one or more recurring units of the Formula (Ia):

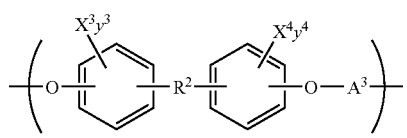
(Ia)

wherein:
$X^3$ and $X^4$ are each independently selected from the group consisting of Br and I;
y3 and y4 are each independently zero or an integer in the range of 1 to 4;
$R^2$ is selected from the group consisting of

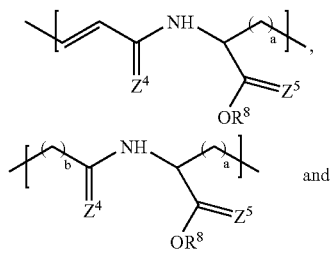

$R^8$ and $R^9$ are each independently H or a non-crystallizable $C_1$ to $C_{30}$ hydrocarbon;
$Z^4$, $Z^5$ and $Z^6$ are each independently O or S;
a and b are each independently an integer in the range of 1 to 8;
$A^3$ is selected from the group consisting of

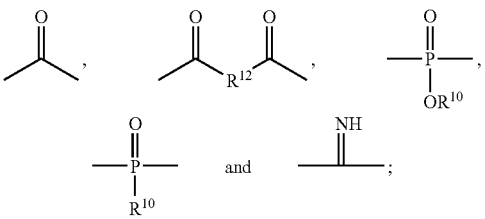

wherein $R^{10}$ is selected from the group consisting of H, $C_1$-$C_{30}$ alkyl, and $C_1$-$C_{30}$ heteroalkyl; and wherein $R^{12}$ is selected from the group consisting of $C_1$-$C_{30}$ alkyl, $C_1$-$C_{30}$ heteroalkyl, $C_5$-$C_{30}$ aryl, $C_6$-$C_{30}$ alkylaryl, and $C_2$-$C_{30}$ heteroaryl. Another embodiment provides a medical device that comprises such a polymer.

Certain halogenated compositional variations of the above-described polymers from TABLE 1 may be represented generically by the Formula (I), as well as other formulas set forth herein. It should be noted that the compositional range described herein for polymers comprising recurring units of the Formula (I) exceeds those described in TABLE 1. Accordingly, some preferred examples of inherently radiopaque, biocompatible, bioresorbable polymers are those comprising recurring units represented by the Formula (I), including polymers that further comprise recurring units of the Formula (Ia) and/or Formula (II).

For example, in accordance with one preferred embodiment of the present invention, a medical device is disclosed, comprising an inherently radiopaque, biocompatible, bioresorbable polymer, including homogeneous polymers, copolymers and blends thereof, wherein the polymer comprises one or more recurring units of the Formula (III):

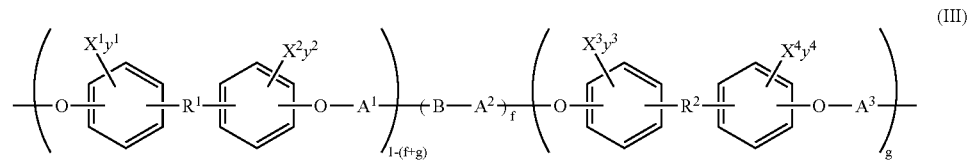
(III)

wherein $X^1$, $X^2$, $X^3$, and $X^4$ are each independently I or Br;
y1, y2, y3, and y4 are each independently 0, 1, 2, 3 or 4;
wherein f and g may range from 0 to 1, with the provisio that the sum of f and g is less than 1;
wherein $R^1$ and $R^2$ are independently:

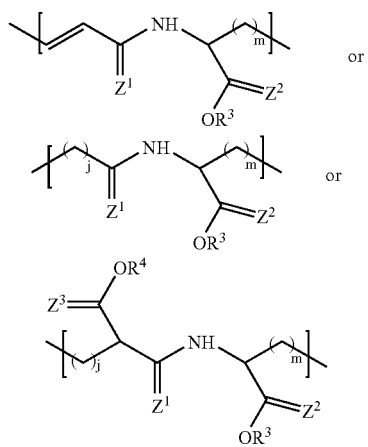

wherein $R^3$ and $R^4$ are each independently H or a non-crystallizable $C_1$ to $C_{30}$ hydrocarbon;
wherein j and m are independently integers from 1 to 8;
wherein $Z^1$, $Z^2$, and $Z^3$ are each independently O or S;
wherein $A^1$ is:

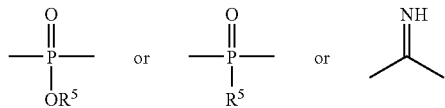

wherein $R^5$ is H or a $C_1$ to $C_{30}$ hydrocarbon;
wherein $A^2$ and $A^3$ are each independently selected from the group consisting of

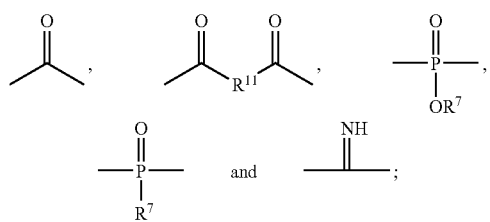

wherein $R^7$ is H or a $C_1$ to $C_{30}$ hydrocarbon and $R^{11}$ is selected from the group consisting of $C_1$-$C_{30}$ alkyl, $C_1$-$C_{30}$ heteroalkyl, $C_5$-$C_{30}$ aryl, $C_6$-$C_{30}$ alkylaryl, and $C_2$-$C_{30}$ heteroaryl;
wherein B is —O—$(CHR^6)_p$—$O)_q$—;
wherein $R^6$ is H or $C_1$ to $C_3$ alkyl; and
wherein p and q are each individually an integer in the range of about 1 to about 100.

Preferably, $X^1$, $X^2$, $X^3$, $X^4$, y1, y2, y3 and y4 are selected so that $X^1$, $X^2$, $X^3$, $X^4$ are present in an amount that is effective to render the polymer radiopaque. For example, in an embodiment, the sum of y1, y2, y3, and y4 is at least one. In another embodiment, B is an aliphatic linear or branched diol or a poly(alkylene glycol) unit. It will be recognized that the recurring unit of the Formula (III) comprises recurring units of the Formulae (I), (II) and (Ia) as described above. Thus, a polymer that comprises a recurring unit of the Formula (III) is an example of the polymer that comprises a recurring unit of the Formula (I).

Halogenation of the aromatic rings may be accomplished as described in the examples below, and by conventional methods as detailed in U.S. Pat. No. 6,475,477; herein incorporated in its entirety by reference and particularly for the purpose of describing methods of halogenating monomers. Preferred polymers are sufficiently halogenated to render the polymers radiopaque, e.g., y1 and y2 in Formula (I) may independently=0, 1, 2, 3 or 4. Halogenation of aromatic rings is preferred. In an embodiment, the sum of y1 and y2 is at least one. Various other groups within the polymer may also be halogenated.

Within the broad class of halogenated polymers comprising recurring units represented by Formula (I), polymers having the $R^1$ and $A^1$ groups indicated in TABLE 2 are preferred:

TABLE 2

| No. | $R^1$ | $A^1$ |
|---|---|---|
| 1 | | |
| 2 | | |
| 3 | | |
| 4 | | |
| 5 | | |
| 6 | | |
| 7 | | |

TABLE 2-continued

| No. | R¹ | A¹ |
|---|---|---|
| 8 | (structure with OR⁴, Z³, Z¹, NH, OR³, Z²) | O=P-R⁵ |
| 9 | (structure with OR⁴, Z³, Z¹, NH, OR³, Z²) | NH= |

According to one aspect of the present invention, a halogen-substituted polymer is provided containing one or more recurring units described by Formula (I). The composition of the halogenated monomers disclosed herein are also included in accordance with preferred embodiments of the present invention. In certain embodiments, polymers comprising a recurring unit of the formula (I) do not contain crystallizable groups, e.g., do not contain crystallizable side chains. For example, in certain embodiments described above, $Q^1$, $Q^2$ and $Q^3$ in the formula for $R^1$ are each independently H or a non-crystallizable group comprising from about 1 to about 30 carbons. In other embodiments described above, $R^3$, $R^4$, $R^8$ and/or $R^9$ are each independently H or a non-crystallizable $C_1$ to $C_{30}$ hydrocarbon. The crystallization of side chains may be minimized or prevented by controlling the length of the side chain, the type of the side chain and the spacing between side chains. As the spacing between side chains increases, the tendency for the side chains to be crystallizable tends to decrease. Likewise, as the flexibility of the side chains increases, the tendency for the side chains to be crystallizable tends to decrease. Similarly, as the length of the side chains decrease, the tendency for the side chains to be crystallizable also tends to decrease. Thus, certain embodiments of polymers comprising a recurring unit of the formula (I) do not inlcude the side chain crystallizable polymers described in U.S. patent application Ser. No. 11/176,638, filed Jul. 7, 2005, which is hereby incorporated by reference in its entirety.

Monomer and Polymer Syntheses: The polymers described herein (including, e.g, polymers comprising a recurring unit of the Formula (I)) may be synthesized by various conventional reactions known in the art. For example, Synthetic Schemes 1-3 illustrate the preparation of halogenated phenolic monomers useful for the making polymers of the Formula (I).

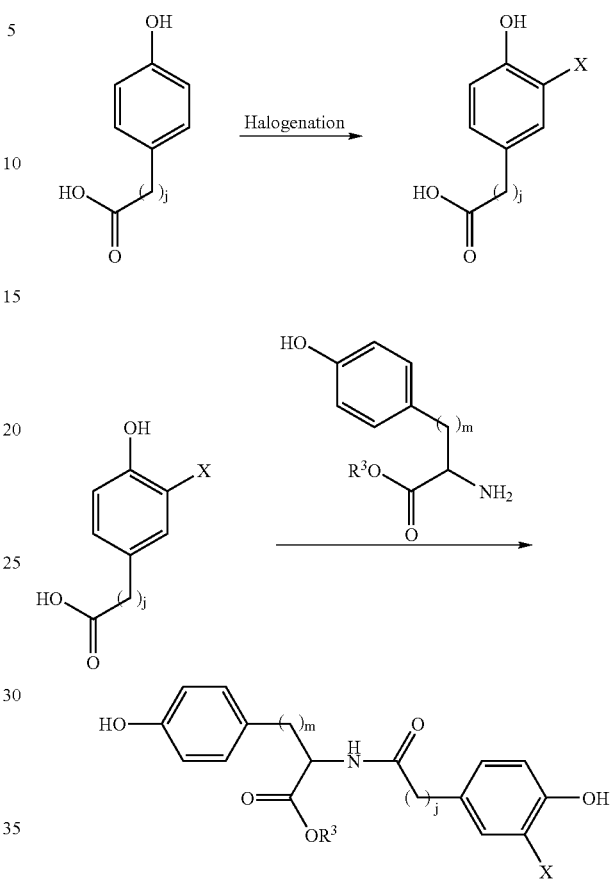

Synthetic Scheme 1

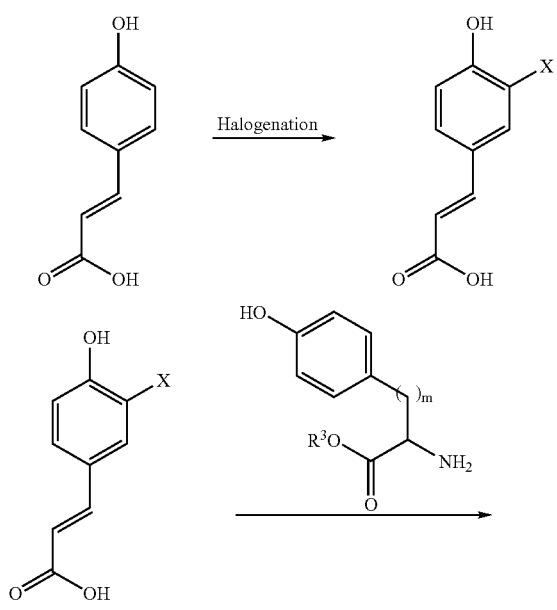

Synthetic Scheme 2

-continued

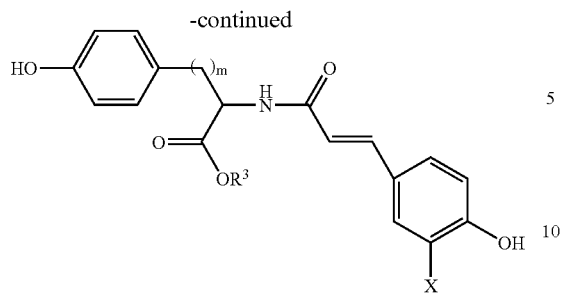

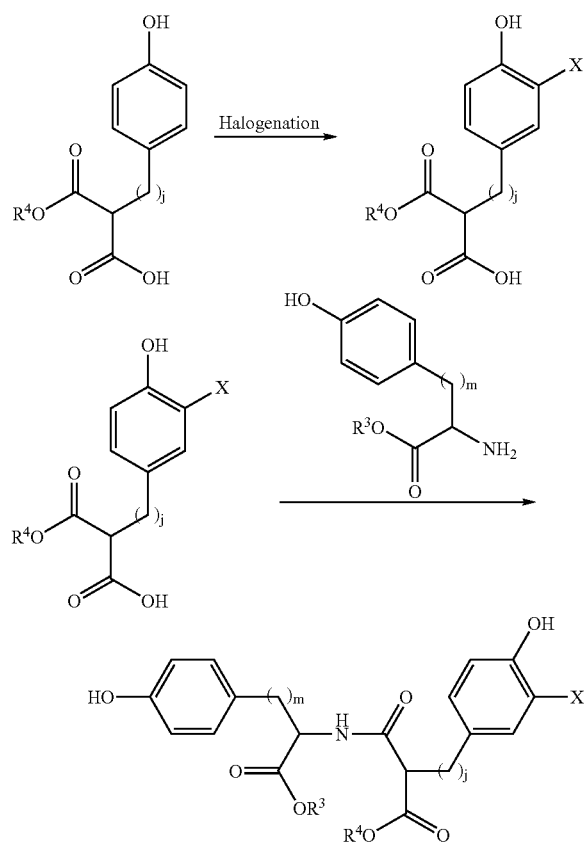

Synthetic Scheme 3

In Synthetic Schemes 1-3 above, X may be a halogen, such as iodo, bromo, chloro, or flouro. Preferably, the halogen is iodo or bromo. Halogenation may be performed by conventional reactions known in the art. For instance, iodination may be performed on aryl rings by treatment with KI, ICl, IF, benzyltrimethylammonium dichloroiodate, or $I_2$ in the presence of copper salts. Likewise, bromination may be performed on aryl rings by treatment with bromine in the presence of a catalyst, such as iron. Other brominating reagents include HOBr and bromo amides. The coupling of the acid and the amine illustrated in Synthetic Schemes 1-3 may also be performed by conventional reactions in known in the art. Standard coupling reagents, including EDCI, HBTU, HOBt, and the like, may be used for activation of the reactants.

The resulting halogenated phenolic monomers may then be polymerized to form various linkages e.g., polymers having phosphate linkages, such as poly(phosphates) and poly(phos-phonates). The respective structures of these classes of polymers, each having a different side chain connected to the phosphorus atom, are as follows:

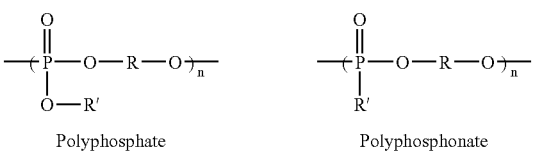

Polyphosphate      Polyphosphonate

The versatility of these polymers may come from the versatility of the phosphorus atom, which is known for a multiplicity of reactions. Its bonding may involve the 3p orbitals or various 3s-3p hybrids; spd hybrids are also possible because of the accessible d orbitals. Thus, the physico-chemical properties of the poly(phosphoesters) may be readily changed by varying either the R or R' group. The biodegradability of the polymer is due primarily to the physiologically labile phosphoester bond in the backbone of the polymer. By manipulating the backbone or the sidechain, a wide range of biodegradation rates are attainable.

Synthetic Schemes 4-5 below illustrate the syntheses of poly(phosphonates) and poly(phosphates), respectively.

Synthetic Scheme 4

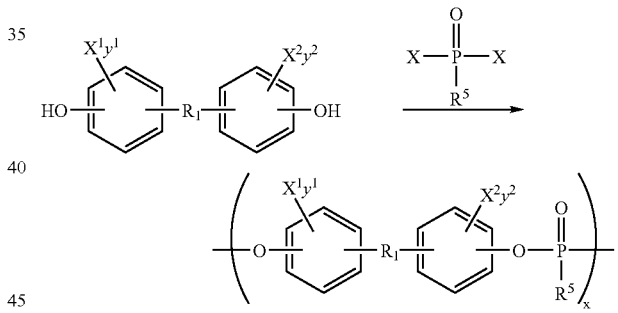

Synthetic Scheme 5

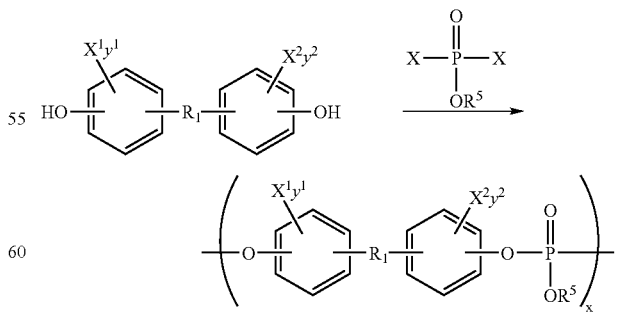

Poly(phosphates) may be prepared by a dehydrochlorination between a phosphodichloridate and a diol according to the following scheme:

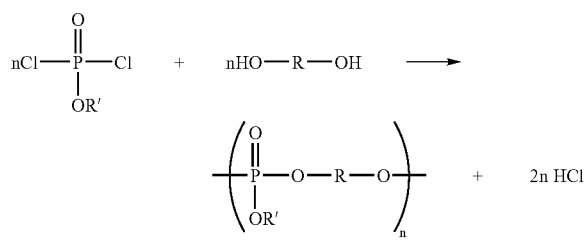

Poly(phosphonates) may be prepared by a similar condensation between appropriately substituted dichlorides and diols.

Poly(phosphites) may be prepared from glycols in a two-step condensation reaction. A 20% molar excess of a dimethylphosphite is preferably used to react with the glycol, followed by the removal of the methoxyphosphonyl end groups in the oligomers by high temperature. An advantage of melt polycondensation is that it avoids the use of solvents and large amounts of other additives, thus making purification more straightforward. It may also provide polymers of reasonably high molecular weight. Polymerization may also be carried out in solution. A chlorinated organic solvent may be used, such as chloroform, dichloromethane, or dichloroethane. To achieve high molecular weights, the solution polymerization is preferably run in the presence of equimolar amounts of the reactants and, more preferably, a stoichiometric amount of an acid acceptor or a Lewis acid-type catalyst. Useful acid acceptors include a tertiary amines such as pyridine or triethylamine. Examples of useful Lewis acid-type catalysts include magnesium chloride and calcium chloride. The product may be isolated from the solution by precipitation in a non-solvent and purified to remove the hydrochloride salt by conventional techniques known to those of ordinary skill in the art, such as by washing with an aqueous acidic solution, e.g., dilute HCl.

Halogenated phenolic monomers may also be polymerized to form polyiminocarbonates as illustrated in Synthetic Scheme 6. Polyiminocarbonates are structurally related to polycarbonates. The polyiminocarbonates have imino groups in the places normally occupied by carbonyl oxygen in the polycarbonates. Thus, the polyiminocarbonates have linkages according to the formula:

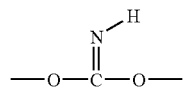

Inclusion of iminocarbonate linkages may impart a significant degree of hydrolytic instability to the polymer. The polyiminocarbonates have desirable mechanical properties akin to those of the corresponding polycarbonates.

Synthetic Scheme 6

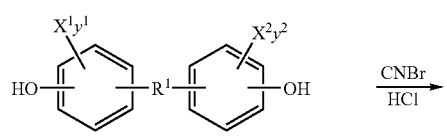

-continued

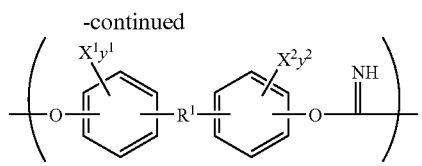

Solution polymerization processes may be used for making polyiminocarbonates. For example, a solution polymerization process may include the steps of contacting a diphenol with a dicyanate in solution in an essentially pure solvent in the presence of a catalyst selected from the group consisting of metal hydroxides, metal hydrides and metal alkoxides and recovering the resulting polyiminocarbonate. The solvent is preferably selected from the group consisting of acetone and tetrahydrofuran ("THF"). Most preferably, the solvent is freshly distilled THF. The catalyst is preferably an alkali metal hydroxide or alkoxide, such as sodium hydroxide or potassium tertbutoxide.

Solvent purity, catalyst selection, and solvent selection may significantly affect the results obtained in the solution polymerization reaction. Thus, even nominally pure reagent-grade or analytical-grade solvents, and particularly THF, may contain residual water, stabilizers such as butylated hydroxy toluene and peroxides. These contaminants, even in minor amounts, may interfere with the solution polymerization reaction. Among the broad class of catalysts suggested for solution polymerization synthesis of polyiminocarbonates, the metal hydroxides, metal alkoxides and metal hydrides, and particularly the alkali metal hydroxides and alkoxides, provide markedly superior results. THF and acetone are preferred solvents.

Interfacial polymerization processes may also be used for production of polyiminocarbonates. For instance, an interfacial polymerization process may include the steps of admixing an aqueous solution of the halogenated phenolic monomer and a basic catalyst with a solution of cyanogen bromide in a water-immiscible organic solvent by progressively adding the aqueous solution to the solution of cyanogen bromide in organic solvent while mixing, and recovering the resulting polyiminocarbonate. The order of addition may be significant, and the rate of addition may also be significant.

The reactions in the above synthetic schemes may be carried through with the non-halogenated versions. Subsequently, halogenation of the polymer may be carried out. Halogenation may be performed by conventional reactions in known in the art. For instance, iodination may be performed on aryl rings by treatment with KI, ICl, IF, benzyltrimethylammonium dichloroiodate, or $I_2$ in the presence of copper salts. For instance, bromination may be performed on aryl rings by treatment with bromine in the presence of a catalyst, such as iron. Other brominating reagents include HOBr and bromo amides. Halogenation of the polymer may be non-selective, which is within the scope of the embodiments.

Starting materials described herein are available commercially, are known, or may be prepared by methods known in the art. Additionally, starting materials not described herein are available commercially, are known, or may be prepared by methods known in the art.

Starting materials may have the appropriate substituents to ultimately give desired products with the corresponding substituents. Alternatively, substituents may be added at any point of synthesis to ultimately give desired products with the corresponding substituents.

The synthetic schemes show methods that may be used to prepare the compounds of preferred embodiments. One skilled in the art will appreciate that a number of different synthetic reaction schemes may be used to synthesize the compounds of preferred embodiments. Further, one skilled in the art will understand that a number of different solvents, coupling agents and reaction conditions may be used in the syntheses reactions to yield comparable results.

One skilled in the art will appreciate variations in the sequence and, further, will recognize variations in the appropriate reaction conditions from the analogous reactions shown or otherwise known which may be appropriately used in the processes above to make the compounds of preferred embodiments.

In the processes described herein for the preparation of the compounds of preferred embodiments, the requirements for protective groups are generally well recognized by one skilled in the art of organic chemistry, and accordingly the use of appropriate protecting groups is necessarily implied by the processes of the schemes herein, although such groups may not be expressly illustrated. Introduction and removal of such suitable protecting groups are well known in the art of organic chemistry; see for example, T. W. Greene, "Protective Groups in Organic Synthesis", Wiley (New York), 1999.

The products of the reactions described herein are isolated by conventional means such as extraction, distillation, chromatography, and the like.

The salts of the compounds of synthetic schemes described above are prepared by reacting the appropriate base or acid with a stoichiometric equivalent of the compounds of synthetic schemes described above.

The polymers described herein, e.g., polymers comprising a recurring unit of the Formula (I), may be used for various applications such as in medical devices. For example, various preferred embodiments provide medical devices that comprise a polymer of the formula (I). The medical device may comprise the polymer in various ways. For example, the medical device may be constructed in whole or in part of the polymer, coated with the polymer, sealed within the polymer, and/or the device may contain the polymer. Non-limiting examples of medical devices that may comprise a polymer of the Formula (I) include for vascular applications a stent, stent graft, annuloplasty ring, vascular graft, suture, vascular cuff, septal defect repair device, heart valve, heart valve component, heart valve repair device, closure device, inducer of vasculature and connective tissue proliferation, and tissue engineered implant. In some embodiments, the medical device does not include any of the medical devices (e.g., embolotherapy products) described in U.S. patent application Ser. No. 10/952,274, filed Sep. 27, 2004, published on May 19, 2005 as U.S. Patent Publication No. 2005/0106119 A1, which is hereby incorporated by reference in its entirety. In some embodiments, the medical device does not include any of the medical devices (e.g., an embolotherapy product) comprising a side chain crystallizable polymer described in U.S. patent application Ser. No. 11/176,638, filed Jul. 7, 2005, which is hereby incorporated by reference in its entirety.

In a preferred embodiment, the medical device comprises a stent. The stent may comprise various configurations, e.g., a configuration selected from the group consisting of a sheet stent, a braided stent, a self-expanding stent, a wire stent, a deformable stent, and a slide-and-lock stent.

In a preferred embodiment, the stent comprises at least two substantially non-deforming elements arranged to form a tubular member, the non-deforming elements being slidably interconnected for allowing the tubular member to expand from a collapsed diameter to an expanded diameter. In another variation the tubular member comprises a series of slideably engaged radial elements and at least one locking mechanism which permits one-way sliding of the radial elements from a first collapsed diameter to a second expanded diameter.

A stent on a catheter is commonly collectively referred to as a stent system. Catheters include but are not limited to over-the-wire catheters, coaxial rapid-exchange designs and the Medtronic Zipper Technology that is a relatively new multi-exchange delivery platform. Such catheters may include, for instance, those described in U.S. Pat. Nos. 4,762,129; 5,232,445; 4,748,982; 5,496,346; 5,626,600; 5,040,548; 5,061,273; 5,350,395; 5,451,233 and 5,749,888. Additional examples of suitable catheter designs include those described in U.S. Pat. Nos. 4,762,129; 5,092,877; 5,108,416; 5,197,978; 5,232,445; 5,300,085; 5,445,646; 5,496,275; 5,545,135; 5,545,138; 5,549,556; 5,755,708; 5,769,868; 5,800,393; 5,836,965; 5,989,280; 6,019,785; 6,036,715; 5,242,399; 5,158,548; and 6,007,545. The disclosures of the above-cited patents are incorporated herein in their entirety by reference thereto.

Catheters may be specialized for various purposes such as to produce an ultrasound effect, electric field, magnetic field, light and/or temperature effect. Heating catheters may include for example those described in U.S. Pat. Nos. 5,151,100, 5,230,349; 6,447,508; and 6,562,021 as well as WO 90\14046 A1. Infrared light emitting catheters may include for example those described in U.S. Pat. Nos. 5,910,816 and 5,423,321. The disclosures of the above-cited patents and patent publications are incorporated herein in their entirety by reference thereto.

In another preferred variation, the stent further comprises an amount of a therapeutic agent (for example, a pharmaceutical agent and/or a biologic agent) sufficient to exert a selected therapeutic effect. The term "pharmaceutical agent", as used herein, encompasses a substance intended for mitigation, treatment, or prevention of disease that stimulates a specific physiologic (metabolic) response. The term "biological agent", as used herein, encompasses any substance that possesses structural and/or functional activity in a biological system, including without limitation, organ, tissue or cell based derivatives, cells, viruses, vectors, nucleic acids (animal, plant, microbial, and viral) that are natural and recombinant and synthetic in origin and of any sequence and size, antibodies, polynucleotides, oligonucleotides, cDNA's, oncogenes, proteins, peptides, amino acids, lipoproteins, glycoproteins, lipids, carbohydrates, polysaccharides, lipids, liposomes, or other cellular components or organelles for instance receptors and ligands. Further the term "biological agent", as used herein, includes virus, serum, toxin, antitoxin, vaccine, blood, blood component or derivative, allergenic product, or analogous product, or arsphenamine or its derivatives (or any trivalent organic arsenic compound) applicable to the prevention, treatment, or cure of diseases or injuries of man (per Section 351(a) of the Public Health Service Act (42 U.S.C. 262(a)). Further the term "biological agent" may include 1) "biomolecule", as used herein, encompassing a biologically active peptide, protein, carbohydrate, vitamin, lipid, or nucleic acid produced by and purified from naturally occurring or recombinant organisms, antibodies, tissues or cell lines or synthetic analogs of such molecules; 2) "genetic material" as used herein, encompassing nucleic acid (either deoxyribonucleic acid (DNA) or ribonucleic acid (RNA), genetic element, gene, factor, allele, operon, structural gene, regulator gene, operator gene, gene complement, genome, genetic code, codon, anticodon, messenger RNA (mRNA), transfer RNA (tRNA), ribosomal extrachromosomal genetic element, plasmagene, plasmid, transposon, gene mutation, gene sequence, exon, intron, and, 3) "processed biologics", as used herein, such as cells, tissues or organs that have undergone manipulation. The therapeutic agent may also include vitamin or mineral substances or other natural elements.

For devices placed in the vascular system, the amount of the therapeutic agent is preferably sufficient to inhibit restenosis or thrombosis or to affect some other state of the stented tissue, for instance, heal a vulnerable plaque, and/or prevent rupture or stimulate endothelialization. The agent(s) may be selected from the group consisting of antiproliferative agents, anti-inflammatory, anti-matrix metalloproteinase, and lipid lowering, cholesterol modifying, anti-thrombotic and antiplatelet agents, in accordance with preferred embodiments of the present invention. In some preferred embodiments of the stent, the therapeutic agent is contained within the stent as the agent is blended with the polymer or admixed by other means known to those skilled in the art. In other preferred embodiments of the stent, the therapeutic agent is delivered from a polymer coating on the stent surface. In another preferred variation the therapeutic agent is delivered by means of no polymer coating. In other preferred embodiments of the stent, the therapeutic agent is delivered from at least one region or one surface of the stent. The therapeutic may be chemically bonded to the polymer or carrier used for delivery of the therapeutic of at least one portion of the stent and/or the therapeutic may be chemically bonded to the polymer that comprises at least one portion of the stent body. In one preferred embodiment, more than one therapeutic agent may be delivered.

An optimized polymer for use in the fabrication of a stent should fulfill at least some of the following criteria:

Radiopacity is preferably sufficient to ensure visibility of the stent structure against the background of a human chest by X-ray fluoroscopy, the standard method used in the clinic.

Stents according to aspects of the present invention are preferably formed with walls for providing a low crossing profile and for allowing excellent longitudinal flexibility. In preferred embodiments, the wall thickness is about 0.0001 inches to about 0.0250 inches, and more preferably about 0.0010 to about 0.0100 inches. However, the wall thickness depends, at least in part, on the selected material. For example, the thickness may be less than about 0.0060 inches for plastic and degradable materials and may be less than about 0.0020 inches for metal materials. More particularly, for a 3.00 mm stent application, when a plastic material is used, the thickness is preferably in the range of about 0.0040 inches to about 0.0045 inches. However, a stent having various diameters may employ different thicknesses for biliary and other peripheral vascular applications. The above thickness ranges have been found to provide preferred characteristics through all aspects of the device including assembly and deployment. However, it will be appreciated that the above thickness ranges should not be limiting with respect to the scope of the invention and that the teachings of the present invention may be applied to devices having dimensions not discussed herein.

The stents are preferably hemocompatible to prevent acute thrombosis. Accordingly, the device surfaces are preferably resistant to protein adsorption and platelet/monocyte attachment. Further, the device surfaces ideally favor endothelial overgrowth but discourage attachment and growth of smooth muscle cells (which are responsible for the occurrence of restenosis).

Stents preferably maintain their mechanical strength (e.g., hoop strength) for a period of about 1-24 months, more preferably about 3-18 months, more preferably still about 3-12 months, and most preferably about 3-6 months.

Stents preferably have a desirable biodegradation and bioresorption profile such that the stents reside for a period of time in the body lumen such that at a later time any stent, bioresorbable or metal or other, may be used to re-treat the approximate same region of the blood vessel or allow for other forms of vessel re-intervention such as vessel bypass.

The term "bioresorbable" is used herein to designate polymer that undergoes biodegradation (through the action of water and/or enzymes to be chemically degraded) and at least some the degradation products are eliminated and/or absorbed by the body. The term "radiopaque" is used herein to designate an object or material comprising the object visible by in vivo analysis techniques for imaging such as, but not limited to, methods such as x-ray radiography, fluoroscopy, other forms of radiation, MRI, electromagnetic energy, structural imaging (such as computed or computerized tomography), and functional imaging (such as ultrasonography). The term, "inherently radiopaque", is used herein to designate a polymer that is intrinsically radiopaque due to the covalent bonding of halogen species to the polymer. Accordingly, the term does not encompass a unhalogenated polymer in which radiopacity is solely due to blending with a halogenated species or other radiopacifying agents such as metals and their complexes.

The highly beneficial combination of properties associated with the preferred halogenated polymers in accordance with embodiments of the present invention are well-suited for use in producing a variety of medical devices besides stents, especially in medical applications whereby the devices and/or applications to treat, repair, reconstruct, cosmetically augment, and heal are preferably radiopaque, biocompatible, and have various times of bioresorption. The invention may be administered in vivo on, in or around a tissue or organ. Likewise it may administered ex vivo onto an excised tissue and organ surface and/or used with another device or device component and then placed into the body. The invention may be administered with other synthetic substrates and/or biologic or engineered substrates and/or therapeutics.

For example, applicants have recognized that, in certain embodiments, in addition to stents, the polymers described herein are suitable for use in producing implantable devices with and without therapeutic agents, device components and/or coatings with and without therapeutic agents for other cardiovascular and peripheral vascular devices (e.g., heart, valves, arterial and venous blood vessels and microvasculature and cardiac muscle). In some preferred embodiments, the present halogenated polymers may be advantageously used in making various products that include therapeutic delivery systems for annuloplasty rings, stent grafts, closure devices, vascular grafts, sutures, and vascular cuffs (external to the vessel used for various reconstructions, repairs or treatments), septal defect repair devices, heart valve components, valves, valve repair devices, and/or heart closure devices (e.g., patent foramen ovale). Another embodiment provides a medical device configured for delivery of at least one therapeutic agent such as stem cells, genetic material, and tissues, wherein the medical device comprises a polymer that comprises a recurring unit of the Formula (I).

Further, the polymers described herein may be used in implantable medical devices with and without therapeutic agents, device components and/or coatings with and without therapeutic agents for use in other medical systems, for instance, the musculoskeletal or orthopedic system (e.g., tendons, ligaments, bone, cartilage skeletal, smooth muscles); the nervous system (e.g., spinal cord, brain, eyes, inner ear); the respiratory system (e.g., nasal cavity and sinuses, trachea, larynx, lungs); the reproductive system (e.g., male or female reproductive); the urinary system (e.g., kidneys, bladder, urethra, ureter); the digestive system (e.g., oral cavity, teeth, salivary glands, pharynx, esophagus, stomach, small intestine, colon), pancreas (exocrine functions, biliary tract, gall bladder, liver, appendix, recto-anal canal); the endocrine system (e.g., pancreas/islets, pituitary, parathyroid, thyroid, adrenal and pineal body), the hematopoietic system (e.g., blood and bone marrow, lymph nodes, spleen, thymus, lymphatic vessels); and, the integumentary system (e.g., skin, hair, nails, sweat glands, sebaceous glands).

Non-limiting examples of medical devices that may comprise a polymer of the Formula (I) include biocompatible orthopedic devices of which examples are described in U.S. Pat. Nos. 6,689,153 B1 and 6,280,473 B1, both of which are hereby incorporated by reference. The polymer embodiments may be used for such as biocompatible pins, screws, sutures, tacks, clamps, and anchors; hip prosthesis and repair components, porous membranes, plates and rails for reconstructive skeletal applications (e.g., maxillofacial fractures, bone fractures, and osteotomies). The plates may be generally H-, O-, T-, L-, X- and/or Y-shaped plates, or other geometries such as triangular and oblong, all of which may be of various profiles and dimensions; designs, profiles and dimensions of such embodiments are described by Sarver et al., in U.S. Pat. No. 5,868,747 which is hereby incorporated by reference. The plates may be preformed with fastener openings or be designed for drilling and securement upon use. Likewise the biocompatible polymers may be used as membranes, fabrics, meshes and fibrous forms of various dimensions, geometries and design for use in any non-embolic application in the body. Non-limiting examples of medical devices that may comprise a polymer of the Formula (I) include a device for reconstruction of a tendon, ligament, joint, ear, nose, and other cartilaginous tissues, vascular and hemostatic closure devices, skin repair and augmentation and wound healing, adhesion barriers and the like. Furthermore embodiments may comprise a polymer of the Formula (I) for use in cosmetic applications (e.g., a tissue filler to minimize wrinkles) and as sealer for instance in vascular and dental indications.

Medical devices that comprise a polymer of the Formula (I) may include one or more additional components. Non-limiting examples of such additional components include, e.g., a supplementary amount of a radiopacifying agent, e.g., selected from the group consisting of iodine, bromine, barium, bismuth, gold, platinum, tantalum, tungsten, and mixtures thereof; a magnetic resonance enhancing agent; and/or an effective amount of at least one therapeutic agent (for example, a pharmaceutical agent and/or a biologic agent) sufficient to exert a selected therapeutic effect (e.g., at least one agent to treat infection (antibiotic and antimicrobial and antiviral), provide local anesthetization, enhance wound healing and the like), depending on the intended application. In a preferred embodiment, at least a portion of the therapeutic agent is contained within the polymeric material. In another embodiment, at least a portion of the therapeutic agent is contained within a coating on the surface of the medical device.

Furthermore, the polymers described herein may also be used for treatment of tumors in any organ and tissue system of the body. Further implantable, radiopaque discs, plugs, and other devices could be used as a "marker" to track treated regions (for instance as in the case of tumor removal). The inherent radiopaque character coupled with the biocompatibility of the polymers allows for their use as an additive to other polymer products to monitor their location and possibly duration by means of radiopacity. For instance, the radiopaque polymer could be used as a marker band on a catheter, a coating on a guide wire, pacemaker lead or any other device requiring radiopacity. The radiopaque polymer may be admixed with non-radiopaque polymers, by means known to those skilled in the art, to create a composite polymer implant with radiopacity.

The polymers described herein may also be used for filling a body space or structure such as a traumatized tissue or organ, a surgical biopsy core which may be small to large, a region created due tumor tissue excision and for tissue and organ enlargement such as in cosmetic applications, breast and penile enhancements. Filling may be done using the polymer inventions in many embodiments for instance by means of halogenated gels, foams, particles, fibers, or solid or semi-solid (e.g., various consistency or as at least partially or wholly porous devices, laminates, and/or composites). The inherent radiopaque character coupled with the biocompatibility of the polymers of this invention may be particularly suitable for treating damaged, destroyed or removed structures which may be created with an injectable polymer or implantable device; such a product could be used to reconstruct papilla of a breast or an external ear as in cancer patients as two examples.

The inherent radiopaque character coupled with the biocompatibility of the polymers described herein may be particularly suitable for orthopedic and spinal applications. These embodiments may be of many forms, for example but not limited to a solid, semi-solid and/or nonsolid form. This allows for rigid forms to provide enough inherent mechanical strength to withstand pressure from adjacent musculature and not collapse whereas the flexible variations may be more ideal for regions of soft tissue repair or motion. Examples of halogenated moldable or preformed devices, gels, slurries putty and clays include internal and external bone fixation devices, bone pins and screws and interference screws, and anchors, wound closure staples, tacks, sutures, membranes and the like; plating systems, spinal fusion devices, bone replacement, prosthetic ligament/tendon repair and replacements, and even for sophisticated treatments using computer aided design to create customized patient specific devices for repair, augmentation or otherwise such as craniofacial plates, chin implant, check bones et cetera. Other examples of embodiments include use of the polymers as an injectable cement, such as for vertebroplasty whereby the injectable seeps through the interstices of bone and becomes embedded between the pores of the trabeculae and hardens thereby increasing bone density. Further the polymer may be used as a putty or paste whereby the polymer is mixed with demineralized bone, gelatin, other biomaterial or substrate with or without a therapeutic (for instance at least one of a growth factor, bone morphogenetic protein, growth hormone, osteogenic growth peptide and the like) which may be useful for bone replacement, reconstruction and repair.

As detailed herein, various methods and techniques may be used to fabricate or manufacture the medical device embodiments of the invention. These include injection molding, laser machining, laser cutting, laser ablation, die-cutting, chemical etching, plasma etching or other methods known in the art which are capable of producing components, and if necessary, assembling the resulting cut portions into devices. The embodiments described may be fabricated into devices using various rapid prototyping (RP) techniques described in U.S.

Pat. Nos. 5,490,962 and 6,530,958 B1 and by Hutmacher et al., (2004) which is hereby incorporated by reference. RP techniques applied to the fabrication of polymer devices may achieve simple and complex geometries. RP methods may be computer automated and integrated with imaging techniques to produce devices that are customized in size and shape to be tailored for specific applications and for individual patients. Such devices may guide cells and tissue during healing. One may also achieve simultaneous addition of cells during the scaffold fabrication with robotic assembly and automated 3D cell encapsulation techniques to develop tissue-engineered constructs with the polymers described herein.

Examples of RP techniques that may be used with polymers described here include: 1) solid free-form fabrication (SFF) (solvent based, solvent-free and aqueous-based systems) that builds parts by selectively adding materials, layer by layer, as specified by a computer program. Each layer represents the shape of the cross-section of the model at a specific level. SFF techniques offer unique ways to precisely control matrix architecture (size, shape, interconnectivity, branching, geometry and orientation) yielding biomimetic structures varying in design and material composition, thereby enhancing control over mechanical properties, biological effects and degradation kinetics of the scaffolds. SFF also allows inclusion of therapeutic agents. 2) Stereolithography (SLA) is a selective laser sintering technique that uses a $CO_2$ laser beam to sinter thin layers of powdered polymeric materials, forming solid 3D objects. 3) 3-D printing (3DP) technology forms devices layer by layer using an 'ink jet' print head and a binder solution deposited onto the powder bed. 4) Shape deposition manufacturing (SDM) involves the fabrication of a layered scaffold in a customized geometry by processing the clinical imaging data and translating it to the desired scaffold layer by a computer-numerically-controlled cutting machine. 5) Extrusion technology-based systems such as fused deposition modelling (FDM), 3-D plotting, multiphase jet solidification (MJS) and precise extrusion manufacturing (PEM) employ extrusion of a material in a layered fashion to build a scaffold. And, 6) solid ground curing (SGC) in designing devices by use of photochemically driven gelation technology of biomacromolecules that are chemically modified with photodimerizable groups. In this later instance the medical device may be partially rather than wholly biodegradable, e.g., if comprising the polymer described herein and one or more of the following photoreactive agents: polyethyleneglycol-based macromers, acrylated polyethyleneglycol derivatives including polyethylene glycol-co-polyhydroxy acid diacrylate and polyethylene glycol-polylysine diacrylate, both of which are end-capped with acryloyl groups.

As detailed herein, various methods and techniques of device delivery may be used for the embodiments of the invention. In certain embodiments, the medical devices described herein are non-embolic devices that do not include the embolic devices described in U.S. application Ser. No. 10/952,274, filed Sep. 27, 2004, published on May 19, 2005 as U.S. Patent Publication No. 2005/0106119 A1, which is hereby incorporated by reference in its entirety. Devices may be configured to be deliverable by physical surgical insertion, catheter, injection, pouring, spraying and/or squirting, extruded through single or multiple ports into a body region of a mammal. Further the devices may be thermally altered (e.g., cold pak, water bath, microwave, hot plates, hotpak, and use of a device such as that described in U.S. Pat. No. 5,263,991 which is hereby incorporated by reference) and formed and shaped by moulding over a form or mandrel and trimmed for use in a body region. Likewise the polymers may be made flowable for delivery into a body region for all non-embolic indications. Devices may placed directly in or on a body tissue or organ for example in subcutaneous and intramuscular tissue.

Promotion or prevention of cell ingrowth or selective integration of cells and matrix to regions of the scaffold may be accomplished by scaffold design. For instance, pore size may regulate which cell types grow into a porous scaffold. Implantable devices or scaffolds may have a pore size of zero microns (non-porous) to microporous (e.g., 1-200 microns) and macroporous (e.g., 200-1000 microns) as we define here for cell and tissue ingrowth. Devices may also be designed with chambers with pores of 1-1000 microns and chambers that are infinitely larger (macroporous chambers pores 1000 microns or greater) for cell and tissue interactions and reconstitution. Further the device may have regions that are wholly porous, partially porous or both. Whang proposes the pore sizes for fibroblast ingrowth between 20 and 125 microns for regeneration of adult mammalian skin, and 100-250 microns for regeneration of bone (Whang et al., 1995). Smooth surfaces versus rough surfaces are known to effect cell metabolism (Salthouse and Matlaga). Further cellular adhesion, alignment and topographical guidance, migration, attachment and proliferation and matrix production may be modified by altering the porosity, surface roughness and texture (e.g., ridges, spiral, geodesic patterns, spheres, grooves, convex, concave (von Recum et al., 1996; Curtis and Clark 1990). Additionally release of a therapeutic, such as a protein, may be controlled by unique microarchitecture (Whang et al., 1996). Generally the larger the pore size, for instance those of 30 or more microns in diameter, there is a likelihood that immune cells may infiltrate the foreign scaffold and capillaries may form.

Such devices of the polymers described herein may have pores, chambers or apertures sufficient in size and distribution to allow and optimize a proliferation of vasculature and connective tissue cells, derived from adjacent hard and soft tissues, to permeate through and substantially into the defect to heal the region. Such devices may be chemically formulated and adapted to be biodegraded in the body within a period of approximately 2 or more months from an initial implantation.

Additionally the polymers described herein may be used for in vitro to develop tissue engineered implants or for use for direct implantation to a body region as a carrier or chamber to deliver cells (e.g., encapsulated islet cells and/or suspended cells), other materials (e.g., therapeutics, biologics) and/or tissue.

Furthermore, the polymers described herein may also be used for soft tissues. Some examples include anti-adhesion barriers for epicardial, abdominal and pelvic adhesions. In another preferred embodiment the polymers described herein may be used as an implantable mesh or substrate for soft organ reconstruction (e.g., intestine, liver, skin) and for topical sealants applied to any device used for implant, and administered to any incision and cauterization.

Moreover the polymers described herein may be used for in vitro as well, for instance, production and engineering of cells and tissues for transplantation, in vitro cell culture studies for cryopreservation, immunomodulation, immunoisolation, studies of cells (mature, differentiated, fetal, pluripotent stem cells) gene therapy, morphogenesis, for use in bioreactors, studies of kinetics, transport, and mechanics of cells, tissue, organs and engineered devices, cell interaction studies with polymers and scaffolds, and polymer biodegradation studies. Additionally the polymers described herein may be used for in vitro diagnostic testing. As a nonlimiting example, the polymer may be used as a support surface for reactive test agents (e.g., therapeutic agent, cells and other biologics).

In light of the disclosure herein, those of skill in the art will be readily able to fabricate a variety of medical devices that comprise one or more of the polymers described herein (e.g., a polymer comprising a recurring unit of the Formula (I)). After polymerization, appropriate work up of the polymers in accordance with preferred embodiments may be achieved by any of a variety of known methods to produce a variety of stents or other medical devices, suitable for various applications. For example, in certain preferred embodiments, the present polymers are shaped into stents via methods comprising extrusion, compression molding, injection molding, solvent casting, spin casting, combinations of two or more thereof, and the like. Further, stents may be comprised of at least one fiber material, curable material, laminated material, and/or woven material.

Such processes may further include two-dimensional methods of fabrication such as cutting extruded sheets of polymer, via laser cutting, etching, mechanical cutting, or other methods, and assembling the resulting cut portions into stents, or similar methods of three-dimensional fabrication of devices from solid forms. In certain other embodiments, the polymers are formed into coatings on the surface of an implantable device, particularly a stent, made either of a polymer of the present invention or another material, such as metal. Such coatings may be formed on stents via techniques such as dipping, spray coating, combinations thereof, and the like.

A stent produced in accordance with preferred aspects of the present invention may be of any design (e.g., slide-and-lock stents, sheet stents (sometimes referred to as jelly-roll stents), deformable stents, and self-expanding stents) suitable for a given application. Preferably, the stents of the present invention are designed to be readily implantable in the artery or tissue of an animal, such as a human, and to be expandable and/or suitable for holding open an artery, after said artery is opened via a medical procedure, such as an angioplasty. Examples of suitable stent designs for use in the present invention include "slide-and-lock" stents, including those disclosed in U.S. Pat. Nos. 6,033,436; 6,224,626 and 6,623,521, and co-pending U.S. patent application Ser. No. 11/016,269 filed Dec. 17, 2004, all of which are incorporated herein by reference.

Other suitable designs adaptable for use herein include those used traditionally in metal and polymeric stents, including various mesh, jelly-roll, sheet, zigzag, and helical coil designs, e.g., the deformable stents by Palmaz such as U.S. Pat. No. 4,733,665 and its successors which have controllable expansion and a portion of the prosthesis that deforms with a force in excess of the elastic limit. Other stent designs include the following designs and their successors: U.S. Pat. No. 5,344,426 by Lau, U.S. Pat. Nos. 5,549,662 and 5,733,328 by Fordenbacher, U.S. Pat. Nos. 5,735,872 and 5,876,419 by Carpenter, U.S. Pat. No. 5,741,293 by Wijay, U.S. Pat. No. 5,984,963 by Ryan, U.S. Pat. Nos. 5,441,515 and 5,618,299 by Khosravi, U.S. Pat. Nos. 5,059,211; 5,306,286 and 5,527,337 by Stack, U.S. Pat. No. 5,443,500 by Sigwart, U.S. Pat. No. 5,449,382 by Dayton, U.S. Pat. No. 6,409,752 by Boatman, and the like.

The polymers described herein are further useful in the production of a wide variety of therapeutic delivery devices. Such devices may be adapted for use with a variety of therapeutics including, for example, pharmaceuticals (i.e., drugs) and/or biological agents as previously defined and including biomolecules, genetic material, and processed biologic materials, and the like. Any number of transport systems capable of delivering therapeutics to the body may be made, including devices for therapeutics delivery in the treatment of cancer, intravascular problems, dental problems, obesity, infection, control of reproduction and the like. In certain embodiments, any of the aforementioned devices described herein may be adapted for use as a therapeutic delivery device (in addition to any other functionality thereof). Controlled therapeutic delivery systems may be prepared, in which a biologically or pharmaceutically active and/or passive agent is physically embedded or dispersed within a polymeric matrix or physically admixed with a polycarbonate or polyarylate of the present invention. Controlled therapeutic delivery systems may also be prepared by direct application of the therapeutic to the surface of a bioresorbable stent device (comprised of at least one of the present polymers) without the use of these polymers as a coating, or by use of other polymers or substances for the coating.

One major advantage of using the radiopaque, bioresorbable polymers described herein in therapeutic delivery applications is the ease of monitoring the release of a therapeutic and the presence of the implantable therapeutic delivery system. Because the radio-opacity of the polymeric matrix is due to covalently attached halogen substituents, the level of radio-opacity is directly related to the residual amount of the degrading therapeutic delivery matrix still present at the implant site at any given time after implantation. In preferred embodiments, the rate of therapeutic release from the degrading therapeutic delivery system will be correlated with the rate of polymer resorption. In such preferred embodiments, the straightforward measurement of the residual degree of radio-opacity will provide the attending physician with a way to monitor the level of therapeutic release from the implanted therapeutic delivery system.

Stent surface coatings using polymers having functional properties that support biological responses: In addition to stents that may deliver a therapeutic agent, for instance delivery of a biological polymer on the stent such as a repellant phosphorylcholine, the stent may be coated with other bioresorbable polymers predetermined to promote biological responses in the vessel lumen desired for certain clinical effectiveness. The coating may be selected from the broad class of any biocompatible bioresorbable polymer which may include any one or combination of halogenated and/or non-halogenated tyrosine-derived polycarbonates, tyrosine-derived polyarylates, poly(ester amides), poly(amide carbonates), trimethylene carbonate, polycaprolactone, polydioxane, polyhydroxybutyrate, poly-hydroxyvalerate, polyglycolide, polylactides and stereoisomers and copolymers thereof, such as glycolide/lactide copolymers. In a preferred embodiment, the stent is coated with a polymer that exhibits a negative charge that repels the negatively charged red blood cells' outer membranes thereby reducing the risk of clot formation. In another preferred embodiment, the stent is coated with a polymer that exhibits an affinity for cells, (e.g., endothelial cells) to promote healing. In yet another preferred embodiment, the stent is coated with a polymer that repels the attachment and/or proliferation of specific cells, for instance arterial fibroblasts and/or smooth muscle cells in order to lessen restenosis and/or inflammatory cells such as macrophages.

Described above are the inherently radiopaque bioresorbable polymer stents of the present invention that may be modified with a coating to achieve functional properties that support biological responses. Likewise, the other aforementioned medical devices and/or device components of inherently radiopaque bioresorbable polymers may also be modified with a coating as previously stated, to achieve functional properties that support biological responses.

Stent Design

Preferred embodiments of the invention described herein relate generally to expandable medical implants for maintaining support of a body lumen. Over the years, a wide variety of stent types have been proposed. Although the structures of stents may vary substantially, virtually all stents are configured to be expandable from a collapsed condition having a small diameter to an expanded condition having a larger diameter. While in the collapsed condition, the stent is delivered usually via catheter through the blood vessel, or other body lumen, to the treatment site. After the treatment site is reached, the stent is radially expanded to an implantable size for supporting the vessel wall. Expansion of the stent from the collapsed condition to the expanded condition may be achieved in a variety of different ways. Various types of stents are described below based on their configurations and means for expansion. For additional information, a variety of stents types are described by Balcon et al., "Recommendations on Stent Manufacture, Implantation and Utilization," European Heart Journal (1997), vol. 18, pages 1536-1547, and Phillips, et al., "The Stenter's Notebook," Physician's Press (1998), Birmingham, Mich.; the disclosures of which are incorporated herein in their entirety by reference.

Balloon expandable stents are manufactured in the collapsed condition and are expanded to a desired diameter with a balloon. During delivery, a balloon expandable stent is typically mounted on the exterior of an inflatable balloon located along the distal end portion of a catheter. After reaching the treatment site, the stent is expanded from the collapsed condition to the expanded condition by inflating the balloon. The stent is typically expanded to a diameter that is greater than or equal to the inner diameter of the body lumen. The expandable stent structure may be held in the expanded condition by mechanical deformation of the stent as taught in, for example, U.S. Pat. No. 4,733,665 to Palmaz. Alternatively, balloon expandable stents may be held in the expanded condition by engagement of the stent walls with respect to one another as disclosed in, for example, U.S. Pat. No. 4,740,207 to Kreamer, U.S. Pat. No. 4,877,030 to Beck et al., and U.S. Pat. No. 5,007,926 to Derbyshire. Further still, the stent may be held in the expanded condition by one-way engagement of the stent walls together with endothelial growth into the stent, as shown in U.S. Pat. No. 5,059,211 to Stack et al.

The term "radial strength," as used herein, describes the external pressure that a stent is able to withstand without incurring clinically significant damage. Due to their high radial strength, balloon expandable stents are commonly used in the coronary arteries to ensure patency of the vessel. During deployment in a body lumen, the inflation of the balloon may be regulated for expanding the stent to a particular desired diameter. Accordingly, balloon expandable stents may be used in applications wherein precise placement and sizing are important. Balloon expandable stents may also be commonly used for direct stenting, wherein there is no predilation of the vessel before stent deployment. Rather, during direct stenting, the expansion of the inflatable balloon dilates the vessel while also expanding the stent.

One of the first self-expanding stents used clinically is the braided "WallStent," as described in U.S. Pat. No. 4,954,126 to Wallsten. The WallStent generally comprises a metallic mesh in the form of a Chinese finger cuff. The cuff provides a braided stent that is not superelastic, but technically still falls in the self-expanding stent family. Another example of a self-expanding stent is disclosed in U.S. Pat. No. 5,192,307 to Wall wherein a stent-like prosthesis is formed of polymeric or sheet metal that is expandable or contractible for placement. The stent may be biased in an open position and lockable in a closed position or, alternatively, may be biased towards a closed position and lockable in an open position. In the former case, a pin may be used to hold the stent in the collapsed condition. The pin is removed to allow the stent to assume the expanded condition. One or more hooks may be formed into the wall for locking the stent. The hooks engage complementary recesses formed in an opposing wall to mechanically interlock the rolled up sheet forming the stent.

Heat expandable stents are similar in nature to self-expanding stents. However, this type of stent utilizes the application of heat to produce expansion of the stent structure. Stents of this type may be formed of a shape memory alloy, such as Nitinol. Still other types of heat expandable stents may be formed with a tin-coated, heat expandable coil. Heat expandable stents may be delivered to the affected area on a catheter capable of receiving a heated fluid. Heated saline or other fluid may be passed through the portion of the catheter on which the stent is located, thereby transferring heat to the stent and causing the stent to expand.

It is desirable that a stent be balloon expandable for providing accurate placement and sizing at a treatment site. It is also desirable that such a stent has sufficient radial strength to maintain patency of the lumen while subjected to substantial external forces. It is also desirable that such a stent be configured to exhibit little or no longitudinal shortening during radial expansion. It is also desirable that such a stent be sufficiently flexible along the longitudinal axis to conform to the curved shape of a body lumen. It is also desirable that such a stent has the capability to conform to the interior of the body lumen.

While various stent configurations, including without limitation, sheet stents, braided stents, self-expanding stents, wire stents, deformable stents, and a slide-and-lock stents, are known in the art, it will be appreciated that the description is illustrative only and should not be construed in any way as limiting the invention. Indeed, the radiopaque, bioresorbable polymers described herein may be applicable to a variety of other stent designs that are known in the art. Furthermore, various applications of the invention, and modifications thereto, which may occur to those who are skilled in the art, are also encompassed by the general concepts described herein.

Some preferred embodiments relate to an expandable slide-and-lock stent having a plurality of modules. The modules have a plurality of sliding and locking elements permitting one-way sliding of the radial elements from a collapsed diameter to an expanded/deployed diameter, but inhibiting radial recoil from the expanded diameter. One advantage is that the stent design elements of the modules and interlocks may be varied to customize the functional features of strength, compliance, radius of curvature at deployment and expansion ratio. In some preferred embodiments, the stent comprises the polymer described in Formula I, such that the stent comprises a radiopaque, bioresorbable material, which is adapted to vanish over time. In some embodiments, the stent serves as a therapeutic delivery platform.

Some embodiments relate to a radially expandable stent used to open, or to expand a targeted area in a body lumen. In some embodiments, the assembled stent comprises a tubular member having a length in the longitudinal axis and a diameter in the radial axis, of appropriate size to be inserted into the body lumen. The length and diameter of the tubular member may vary considerably for deployment in different selected target lumens depending on the number and configuration of the structural components, described below. The tubular member is adjustable from at least a first collapsed diameter to at least a second expanded diameter. One or more stops and engaging elements or tabs are incorporated into the structural components of the tubular member whereby recoil (i.e., collapse from an expanded diameter to a more collapsed diameter) is minimized to less than about 5%.

The tubular member in accordance with some embodiments has a "clear through-lumen," which is defined as having no structural elements protruding into the lumen in either the collapsed or expanded diameters. Further, the tubular member has smooth marginal edges to minimize the trauma of edge effects. The tubular member is preferably thin-walled (wall thickness depending on the selected materials ranging from less than about 635 to less than about 100 micrometers) and flexible (e.g., less than about 0.01 Newtons force/millimeter deflection) to facilitate delivery to small vessels and through tortuous vasculature. The thin walled design will also minimize blood turbulence and thus risk of thrombosis. The thin profile of the deployed tubular member in accordance with some embodiments also facilitates more rapid endothelialization of the stent.

The wall of the tubular member may comprise at least one module, which comprises a series of sliding and locking radial elements. Preferably, a plurality of modules are connected in the longitudinal axis via linkage elements which couple at least some of the radial elements between adjacent modules. The radial elements are preferably configured within each module so as to define the circumference of the tubular member. Each radial element within a module is preferably a structurally discrete, unitary structure, which is physically separate from other radial elements within the module, and comprises one or more circumferential ribs bowed in the radial axis to form a fraction of the total circumference of the tubular member. At least one of the ribs in each radial element has one or more stops disposed along the length of the rib. At least some of the radial elements also have at least one articulating mechanism for slideably engaging the rib(s) from adjacent, circumferentially offset radial elements. In one aspect of the invention, the articulating mechanism includes a tab for engaging the stops disposed along the slideably engaged adjacent rib. The articulating between the tab from one radial element and the stops from an adjacent radial element is such that a locking or ratcheting mechanism is formed, whereby the adjacent radial elements may slide circumferentially apart from one another, but are substantially prevented from sliding circumferentially toward one another. Accordingly, the tubular member may be radially expanded from a smaller diameter to a larger diameter, but recoil to a smaller diameter is preferably minimized by the locking mechanism.

Other preferred embodiments of slide-and-lock stents, include, but are not limited to, a non-actuating slide-and-lock stent with radial elements following a defined path geometry having both radial and axial translation; a slide-and-lock stent with longitudinal modules comprising both active (slide-and-lock) and passive radial elements wherein the radial elements have a variety of features including, but not limited to, spring elements, frangible deployment control mechanism and device overextension safety catches; a slide-and-lock stent with non-symmetric lockout geometries for enhanced sizing resolution; an actuating slide-and-lock stent with a positive lockout mechanism return; an actuating slide-and-lock stent with an active lockout system; a deformable slide-and-lock stent which provides additional device radial expansion and/or increases device safety; a slide-and-lock stent with two sided lockout features; a crimpable slide-and-lock stent for enhanced retention on a delivery balloon; and a slide-and-lock stent with optimized strut or wall configuration to reduce turbulence and create generally laminar flow of the blood. Further embodiments include a slide-and-lock stent with a region with a high surface area region for support; a slide-and-lock stent with a region with a side-branch vessel access port; and, a slide-and-lock stent with a graft covering. Further embodiments include a slide-and-lock stent comprised of layered materials and/or spatially localized materials.

With reference now to FIG. 1, a portion of a preferred stent embodiment 320 is illustrated wherein radial elements 320(1), 320(2) are slidably interconnected. Each radial element is provided with a rail 328 having a plurality of deflectable teeth 326. Each of the teeth is angled upward and is configured to deflect downward (i.e., in a radial direction). As the locking tabs 322, 324 slide along the deflectable teeth 326, the teeth are caused to deflect downward for allowing the tabs 322, 324 to pass over the teeth 326 during deployment. However, due to the angle of the teeth, the locking tabs may only move in one direction. More particularly, if a compressive force pushes the radial elements 320(1), 320(2) back toward the collapsed condition, the locking tabs 322, 324 will abut against the teeth 326, thereby preventing further relative movement.

Some aspects of additional embodiments of stents are disclosed in U.S. Pat. Nos. 6,033,436, 6,224,626 and 6,623,521 and co-pending U.S. application Ser. No. 10/897,235 filed on Jul. 21, 2004 and Ser. No. 11/016,269 filed on Dec. 17, 2004; all of which are hereby incorporated in their entirety by reference thereto.

Although a stent formed from a single integral element is described above as having particular mechanical characteristics for locking the stent in the expanded condition, a variety of other "slide and lock" mechanisms may be used. For example, other suitable locking mechanism may be found in U.S. Pat. No. 5,344,426 to Lau, U.S. Pat. Nos. 5,735,872 and 5,876,419 to Carpenter, U.S. Pat. No. 5,741,293 to Wijay, U.S. Pat. No. 5,984,963 to Ryan, U.S. Pat. Nos. 5,441,515 and 5,618,299 by Khosravi, U.S. Pat. No. 5,306,286 to Stack, U.S. Pat. No. 5,443,500 to Sigwart, U.S. Pat. No. 5,449,382 to Dayton, U.S. Pat. No. 6,409,752 to Boatman, and the like. Each of these references is incorporated by reference herein. In addition, many of the slide and lock mechanisms disclosed in the above patents may be suitable for use with stents embodiments comprising slidable interconnected elements of the type described above.

Stents that Deliver Therapeutic Agents

Therapeutic agents may be incorporated into the bioresorbable stent and/or coated on at least one region of the stent surface, thereby providing local release of such agents. In preferred embodiments, the therapeutic agent is contained within the stent as the agent is blended with the polymer or admixed by other means known to those skilled in the art. In other preferred embodiments of the stent, the therapeutic agent is delivered from a polymer coating on the stent surface. In another preferred variation the therapeutic agent is delivered by means of no polymer coating. In other preferred embodiments of the stent, the therapeutic agent is delivered from at least one region or one surface of the stent.

The preferred therapeutic agent(s) control restenosis (including neointimal thickening, intimal hyperplasia and in-stent restenosis or limits vascular smooth muscle cell overgrowth) in the lumen of a stented vessel. Vascular stent applications and other body applications may require a different therapeutic or more than one therapeutic.

A variety of compounds are considered to be useful in controlling vascular restenosis and in-stent restenosis. Some of these preferred agents that improve vascular patency include without limitation paclitaxel, Rapamycin, ABT-578, everolimus, dexamethasone, nitric oxide modulating molecules for endothelial function, tacrolimus, estradiol, mycophenolic acid, C6-ceramide, actinomycin-D and epothilones, and derivatives and analogs of each.

The preferred therapeutic agent may also limit or inhibit thrombosis or affect some other state of the stented tissue, for instance, heal a vulnerable plaque, inhibit plaque rupture, stimulate endothelialization or limit other cell types from proliferating and from producing and depositing extracellular matrix molecules. The agent(s) may be selected from the group consisting of but not limited to: antiproliferative agents, anti-inflammatory, anti-matrix metalloproteinase, and lipid lowering, anti-thrombotic and antiplatelet agents, in accordance with preferred embodiments of the present invention.

In a preferred stent embodiment the device delivers a therapeutic agent(s) to treat the vulnerable plaque lesion such as an anti-inflammatory, a lipid lowering/matrix altering therapeutic and/or an antiproliferative. The anti-inflammatory may include aspirin, an effective neutralizer of inflammation, losartan, an angiotensin receptor blocker or pravastatin, a 3-Hydroxy-3-Methyl-Glutaryl Coenzyme A (HMG-CoA) reductase inhibitor. Further delivery of statins, such as pravastatin and fluvastatin, which are 3-HMG-CoA reductase inhibitors may interstitial collagen gene expression and lower matrix metalloproteinases (MMP-1, MMP-3, and MMP-9) expression to effectively stabilize the vulnerable plaque lesions. Local stent delivery of lipid-lowering agent, for example Pravastatin, may also improve plaque stability.

In a preferred stent embodiment the device delivers an antiplatelet agent that acts by glycoprotein IIb/IIIa receptor inhibition or other means such as but not limited to aspirin, Plavix (clopidogrel bisulfate), ticlopidine, integrelin, and dipyridamole. In another preferred stent embodiment the device delivers an antithrombin agent that acts by thrombin inhibition or other means such as heparin, low molecular weight heparin (LMWH), polyamine to which dextran sulfate and heparin are covalently bonded, heparin-containing polymer coating for indwelling implants (MEDI-COAT by STS Biopolymers), polyurethane urea/heparin, R-Hirudin, Hirulog, hirudin/prostacyclin and analogues, argatroban, efegatran, and tick anticoagulant peptide. Additional anti-thrombogenic substances and formulations may include but are not limited to endothelium-derived relaxing factor, prostaglandin I.sub.2, plasminogen activator inhibitor, tissue-type plasminogen activator (tPA), ReoPro: anti-platelet glycoprotein IIb/IIIa integrin receptor, fibrin and fibrin peptide A, lipid-lowering drugs, e.g., Omega-3 fatty acids, and Chrysalin (aka TRAP-508) by Chrysalis Vascular Technologies.

Various compounds address other pathologic events and/or vascular diseases. Some of these therapeutic target compounds are agents to treat endothelial injury (e.g., VEGF; FGF), agents to modulate cell activation and phenotype (e.g., MEF-2 & Gax modulators; NFKB antagonists; cell cycle inhibitors), agents for dysregulated cell growth (e.g., E2F decoys; RB mutants; cell cycle inhibitors), agents for dysregulated apoptosis (e.g., Bax or CPP32 inducers; Bcl-2 inhibitors; integrin antagonists) and agents for abnormal cell migration (e.g., integrin antagonists; PDGF blockers; plasminogen activator inhibitors).

The therapeutic agents to be coated or incorporated within the stent polymer of embodiments of the invention may be classified in terms of their sites of action in the host. The following agents are believed to exert their actions extracellularly or at specific membrane receptor sites. These include corticoids and other ion channel blockers, growth factors, antibodies, receptor blockers, fusion toxins, extracellular matrix proteins, peptides, or other biomolecules (e.g., hormones, lipids, matrix metalloproteinases, and the like), radiation, anti-inflammatory agents including cytokines such as interleukin-1 (IL-1), and tumor necrosis factor alpha (TNF-α), gamma interferon (interferon-γ), and Tranilast, which modulate the inflammatory response.

Other groups of agents exert their effects at the plasma membrane. These include those involved in the signal transduction cascade, such as coupling proteins, membrane associated and cytoplasmic protein kinases and effectors, tyrosine kinases, growth factor receptors, and adhesion molecules (selectins and integrins).

Some compounds are active within the cytoplasm, including for example, heparin, ribozymes, cytoxins, antisense oligonucleotides, and expression vectors. Other therapeutic approaches are directed at the nucleus. These include gene integration, proto-oncogenes, particularly those important for cell division, nuclear proteins, cell cycle genes, and transcription factors.

Other therapeutic substances that may be useful as stent coatings and/or depot formulations incorporated within bioresorbable stents include: antibodies e.g., ICAM-1 antibodies for inhibition of monocyte chemotactic recruitment and adhesion, macrophage adhesion and associated events (Yasukawa et al, 1996, Circulation); toxin based therapies such as chimeric toxins or single toxins to control vascular SMC proliferation (Epstein et al., 1991, Circulation); bFGF-saporin to selectively stop SMC proliferation among those cells with a large number of FGF-2 receptors (Chen et al, 1995, Circulation), suramin inhibits migration and proliferation by blocking PDGF-induced and/or mitogen activated protein kinase (MAPK-AP-1)-induced signaling (Hu et al, Circulation, 1999); Beraprost Sodium, a chemically stable prostacyclin analogue ($PGI_2$), suppresses intimal thickening and luminal narrowing of coronary arteries. (Kurisu et al., Hiroshima J. Med Sci, 1997); Verapamil inhibits neointimal smooth muscle cell proliferation (Brauner et al., J Thorac Cardiovasc Surg 1997), agents that block the CD 154 or CD40 receptor may limit the progression of atherosclerosis (E Lutgens et al., Nature Medicine 1999), agents that control responses of shear stress response elements or mechanical stress or strain elements or heat shock genes; and anti-chemoattractants for SMC and inflammatory cells.

In addition or in the alternative, cells could be encapsulated in a bioresorbable microsphere, or mixed directly with polymer, or hydrogel. Living cells could be used to continuously deliver molecules, for instance, cytokines and growth factors. Cells of any origin may be used in accordance with this aspect of the present invention. Further, nonliving cells may be used and preserved or dehydrated cells which retain their purpose when rehydrated may be used. Native, chemically modified (processed), and/or genetically engineered cells may be used.

Therapeutic agents may be polar or possess a net negative or positive or neutral charge; they may be hydrophobic, hydrophilic or zwitterionic or have a great affinity for water. Release may occur by controlled release mechanisms, diffusion, interaction with another agent(s) delivered by intravenous injection, aerosolization, or orally. Release may also occur by application of a magnetic field, an electrical field, or use of ultrasound.

In another aspect of the invention, the stent may also incorporate or deliver a hydrogel or other material such as phosphorylcholine (PC) that acts to prevent adhesions of blood cells, blood proteins or blood molecules, extracellular matrix or other cell types. The hydrogel may deliver a therapeutic agent.

Use of synthetic, natural (plant, microbial, viral or animal-derived) and recombinant agents having selected functions or chemical properties may be mixed with complementary substances (e.g., anti-thrombotic and anti-restenosis substances;

nucleic acids and lipid complexes). Pharmacologic agents may also incorporate use of vitamins or minerals. For instance, those that function directly or indirectly through interactions or mechanisms involving amino acids, nucleic acids (DNA, RNA), proteins or peptides (e.g., RGD peptides), carbohydrate moieties, polysaccharides, liposomes, or other cellular components or organelles for instance receptors and ligands.

Genetic approaches to control restenosis include without limitation: use of antisense oligonucleotides to PDGFR-ββ mRNA to control PDGF expression; use of antisense oligonucleotides for nuclear antigens c-myb or c-myc oncogenes (Bauters et al., 1997, Trends CV Med); use of antisense phosphorothioate oligodeoxynucleotides against cdk 2 kinase (cyclin dependent kinase) to control the cell cycle of vascular smooth muscle cells (Morishita et al, 1993, Hypertension); use of VEGF gene (or VEGF itself) to stimulate reconstructive wound healing such as endothelialization and decrease neointima growth (Asahara et al 1995); delivery of the nitric oxide synthetase gene (eNOS) to reduce vascular smooth muscle cell proliferation (Von Der Leyen et al., 1995, Proc Natl Acad Sci); use of adenovirus expressing plasminogen activator inhibitor-1 (PAI-1) to reduce vascular smooth muscle cell migration and thereby diminish restenosis (Carmeliet et al., 1997, Circulation); stimulation of apolipoprotein A-1 (ApoAl) over-expression to rebalance serum levels of LDL and HDL; use of apoptosis gene products to promote cell death (e.g., of smooth muscle cells) and cytotactic gene products to that regulate cell division (tumor suppressor protein p53 and Gax homeobox gene product to suppress ras; p21 over expression); and inhibition of NF-κB activation (e.g., p65) to control smooth muscle cell proliferation (Autieri et al., 1994, Biochem Biophys Res Commun).

Described above are the inherently radiopaque bioresorbable polymer stents of the present invention that deliver a therapeutic agent. Likewise, the other aforementioned medical devices and/or device components of inherently radiopaque bioresorbable polymers may also deliver a therapeutic agent as previously stated.

In addition to their usefulness in medical devices, the polymers described herein may also be useful for in vitro testing, diagnostics and production with cells, tissue, and/or organs and bioengineered materials.

EXAMPLE 1

Syntheis of (3-(3-iodo-4-hydroxyphenyl)propanoic Acid-tyrosine Ethyl Ester)

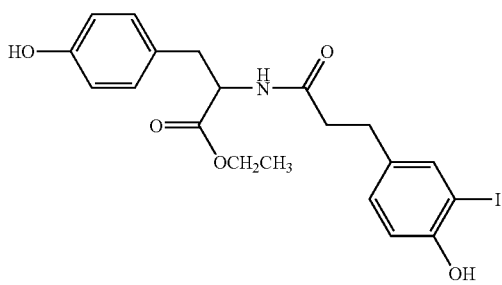

Monomer (3-(3-iodo-4-hydroxyphenyl)propanoic acid tyrosine ethyl ester) is a bisphenol carrying one iodine atom at position 3 of one of the two phenolic rings. This bifunctional molecule may be polymerized as illustrated in subsequent Examples. This Example describes a method used to introduce the iodine atom in the aromatic ring of (4-hydroxyphenyl)propanoic acid, and the coupling of this iodinated derivative with tyrosine ethyl ester in order to obtain 3-(3-iodo-4-hydroxyphenyl)propanoic acid-tyrosine ethyl ester).

Iodination of 3-(4-hydroxyphenyl)propanoic acid

Preparation of solution (a): to a 250 mL Erlenmeyer flask is added 100 mL of distilled water, 24 g of potassium iodide, and 25 g of iodine. The mixture is stirred overnight until all solids dissolved.

Preparation of solution (b): 16.6 g (0.1 mole) of (4-hydroxyphenyl)propanoic acid is placed in a 3-necked Morton-type round bottom flask, equipped with an overhead mixer and a 125 mL addition funnel. 140 mL of 40% trimethylamine solution in water is added, and the mixture is stirred until a clear solution is obtained.

Solution (a) is placed in the addition funnel, and added dropwise to solution (b) while vigorously stirring. Addition of each drop of solution (a) imparts a brown color to the reaction mixture. The rate of addition is such that all the color disappears before the next drop is added. Stirring is continued for one hour after the last addition, then 50 mL of sodium thiosulfate 0.1 M is added to the reaction vessel. The same solution is also used to wash the addition funnel.

37% HCl is added dropwise with vigorous mixing until the solution is slightly acidic to litmus, and a solid formed. The mixture is concentrated to half its volume by rotary evaporation, and then it is extracted with ether. The organic phase is dried over magnesium sulfate, and decolorized using animal charcoal. The slurry is then filtered through a small layer of silica gel, and evaporated to dryness. The white solid is recrystallized twice in toluene, recovered by filtration, dried under a stream of nitrogen, and then under high vacuum.

Characterization: DSC analysis shows a melting point range of 109-111° C. $^1$H-NMR (D)MSO) of the product shows the following peaks (ppm): 2.5 (t, 2H), 2.7 (t, 2H), 6.8 (d, 2H), 7.06 (d, 2H), 10.08 (s, 1H), 12.05 (s, 1H). Reverse-phase HPLC shows 3.8% of the starting material, and 1.4% of diiodinated product.

Step 2: Preparation of (3-(3-iodo-4-hydroxyphenyl)propanoic acid-tyrosine ethyl ester)

To a 250 mL 3-necked round bottomed flask equipped with an overhead stirrer is added 17.0 g (0.0582 moles) of 3-(3-iodo-4-hydroxyphenyl)propanoic acid, 12.25 g (0.0585 moles) of tyrosine ethyl ester, and 25 mL of N-methyl-2-pyrrolidinone (NMP). The mixture is stirred until a clear solution is obtained. The flask is cooled in an ice-water bath, then 11.84 g (0.0619 moles) of 1-(3-dimethylaminopropyl)-3-ethylcarbodiimide hydrochloride (EDCI HCl) is added in one portion, followed by 15 mL of NMP. The cooling bath is removed after 2.5 hours, and the reaction is allowed to continue overnight at room temperature. 71 mL of ethyl acetate is added, and stirring is maintained for 15 more minutes. The crude is then transferred into a 500 mL separatory funnel, and extracted once with 75 mL of brine, then with two aliquots (75 and 35 mL) of 3% NaHCO$_3$/14% NaCl, followed by 35 mL aliquots of 0.4M HCl/14% NaCl, and finally with brine. The organic phase is dried over magnesium sulfate and treated with activated carbon, filtered and concentrated to a thick syrup, which crystallizes into a solid mass after a few hours. The product is triturated in methylene chloride using mechanical stirring, then it is recovered by filtration and dried under a nitrogen stream followed by high vacuum.

Characterization: DSC analysis shows a melting point range of 110-113° C. $^1$H-NMR (DMSO) shows the following peaks (ppm): 1.1 (t, 3H), 2.35 (t, 2H), 2.65 (m, 2H), 2.85 (m, 2H), 4.05 (q, 2H), 4.35 (m, 1H), 6.65/6.75/6.95 (m, 6H), 7.5

(s, 1H), 8.25 (d, 1H), 9.25 (s, 1H), 10.05 (s, 1H). Reverse-phase HPLC shows 2.2% of the non-iodinated monomer, and no diiodinated product.

EXAMPLE 2

Syntheis of (3-(3-iodo-4-hydroxyphenyl)-2-propenoic Acid-tyrosine Ethyl Ester)

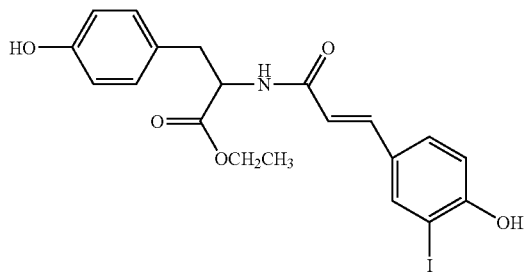

Monomer (3-(3-iodo-4-hydroxyphenyl)-2-propenoic acid-tyrosine ethyl ester) is a bisphenol carrying one iodine atom at position 3 of one of the two phenolic rings. This bifunctional molecule may be polymerized as illustrated in the subsequent Examples. This Example describes a method that may be used to introduce the iodine atom in the aromatic ring of (3-(4-hydroxyphenyl)-2-propenoic acid, and the coupling of this iodinated derivative with tyrosine ethyl ester in order to obtain (3-(3-iodo-4-hydroxyphenyl)-2-propenoic acid-tyrosine ethyl ester).

Iodination of (3-(4-hydroxyphenyl)-2-propenoic acid

Preparation of solution (a): to a 250 mL Erlenmeyer flask may be added 100 mL of distilled water, 24 g of potassium iodide, and 25 g of iodine. The mixture may be stirred overnight until all solids dissolved.

Preparation of solution (b): 16.6 g of (3-(4-hydroxyphenyl)-2-propenoic acid may be placed in a 3-necked Morton-type round bottom flask, equipped with an overhead mixer and a 125 mL addition funnel. 140 mL of 40% trimethylamine solution in water may be added, and the mixture may be stirred until a clear solution is obtained.

Solution (a) may be placed in the addition funnel, and added dropwise to solution (b) while vigorously stirring. Addition of each drop of solution (a) may impart a brown color to the reaction mixture. The rate of addition may be such that all the color disappeared before the next drop is added. Stirring may be continued for one hour after the last addition, the 50 mL of sodium thiosulfate 0.1 M may be added to the reaction vessel. The same solution may also be used to wash the addition funnel.

37% HCl may be added dropwise with vigorous mixing until the solution is slightly acidic to litmus, and a solid formed. The mixture may be concentrated to half its volume by rotary evaporation, and then it may be extracted with ether. The organic phase may be dried over magnesium sulfate, and decolorized using animal charcoal. The slurry may then be filtered through a small layer of silica gel, and evaporated to dryness. The white solid may be recrystallized twice in toluene, recovered by filtration, dried under a stream of nitrogen, and then under high vacuum.

Step 2: Preparation of (3-(3-iodo-4-hydroxyphenyl)-2-propenoic acid-tyrosine ethyl ester)

To a 250 mL 3-necked round bottomed flask equipped with an overhead stirrer may be added 17.0 g of 3-(3-iodo-4-hydroxyphenyl)-2-propenoic acid, 12.25 g (0.0585 moles) or tyrosine ethyl ester, and 25 mL of NMP. The mixture may be stirred until a clear solution is obtained. The flask may be cooled in an ice-water bath, the 11.84 g (0.0619 moles) of EDCI HCl may be added in one portion, followed by 15 mL of NMP. The cooling bath may be removed after 2.5 hours, and the reaction may be allowed to continue overnight at room temperature. 71 mL of ethyl acetate may be added, and stirring may be maintained for 15 more minutes. The crude may then be transferred into a 500 mL separatory funnel, and extracted once with 75 mL of brine, then with two aliquots (75 and 35 mL) of 3% $NaHCO_3$/14% NaCl, followed by 35 mL aliquots of 0.4M HCl/14% NaCl, and finally with brine. The organic phase may be dried over magnesium sulfate and treated with activated carbon, filtered and concentrated to a thick syrup, which may crystallize into a solid mass after a few hours. The product may be triturated in methylene chloride using mechanical stirring, then it may be recovered by filtration and dried under a nitrogen stream followed by high vacuum.

EXAMPLE 3

Synthesis of (2-(3-iodo-4-hydroxybenzyl)methyl Malonate-tyrosine Ethyl Ester)

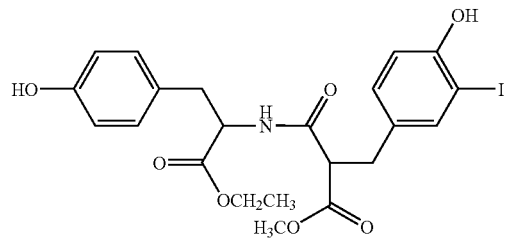

Monomer (2-(3-iodo-4-hydroxybenzyl)methyl malonate tyrosine ethyl ester) is a bisphenol carrying one iodine atom at position 3 of one of the two phenolic rings. This bifunctional molecule may be polymerized as illustrated in the subsequent Examples. This Example describes a method that may be used to introduce the iodine atom in the aromatic ring of (2-(4-hydroxybenzyl)methyl malonate and the coupling of this iodinated derivative with tyrosine ethyl ester in order to obtain (2-(3-iodo-4-hydroxybenzyl)methyl malonate-tyrosine ethyl ester).

Iodination of 2-(4-hydroxybenzyl)methyl malonate

Preparation of solution (a): to a 250 mL Erlenmeyer flask may be added 100 mL of distilled water, 24 g of potassium iodide, and 25 g of iodine. The mixture may be stirred overnight until all solids dissolved.

Preparation of solution (b): 22 g of 2-(4-hydroxybenzyl) methyl malonate may be placed in a 3-necked Morton-type round bottom flask, equipped with an overhead mixer and a 125 mL addition funnel. 140 mL of 40% trimethylamine solution in water may be added, and the mixture may be stirred until a clear solution is obtained.

Solution (a) may be placed in the addition funnel, and added dropwise to solution (b) while vigorously stirring. Addition of each drop of solution (a) may impart a brown color to the reaction mixture. The rate of addition may be such that all the color disappeared before the next drop is added. Stirring may be continued for one hour after the last addition, the 50 mL of sodium thiosulfate 0.1 M may be added to the reaction vessel. The same solution may also be used to wash the addition funnel.

37% HCl may be added dropwise with vigorous mixing until the solution is slightly acidic to litmus, and a solid formed. The mixture may be concentrated to half its volume by rotary evaporation, and then it may be extracted with ether. The organic phase may be dried over magnesium sulfate, and decolorized using animal charcoal. The slurry may then be filtered through a small layer of silica gel, and evaporated to dryness. The white solid may be recrystallized twice in toluene, recovered by filtration, dried under a stream of nitrogen, and then under high vacuum.

Step 2: Preparation of (2-(3-iodo-4-hydroxybenzyl)methyl malonate-tyrosine ethyl ester)

To a 250 mL 3-necked round bottomed flask equipped with an overhead stirrer may be added 23 g of 2-(3-iodo-4-hydroxybenzyl)methyl malonate, 12.25 g (0.0585 moles) or tyrosine ethyl ester, and 25 mL of NMP. The mixture may be stirred until a clear solution is obtained. The flask may be cooled in an ice-water bath, the 11.84 g (0.0619 moles) of EDCI HCl may be added in one portion, followed by 15 mL of NMP. The cooling bath may be removed after 2.5 hours, and the reaction may be allowed to continue overnight at room temperature. 71 mL of ethyl acetate may be added, and stirring may be maintained for 15 more minutes. The crude may then be transferred into a 500 mL separatory funnel, and extracted once with 75 mL of brine, then with two aliquots (75 and 35 mL) of 3% $NaHCO_3$/14% NaCl, followed by 35 mL aliquots of 0.4M HCl/14% NaCl, and finally with brine. The organic phase may be dried over magnesium sulfate and treated with activated carbon, filtered and concentrated to a thick syrup, which crystallized into a solid mass after a few hours. The product may be triturated in methylene chloride using mechanical stirring, then it may be recovered by filtration and dried under a nitrogen stream followed by high vacuum.

EXAMPLE 4

Poly(3-(3-iodo-4-hydroxyphenyl)propanoic Acid-tyrosine Ethyl Ester) by Solution Polymerization with EOP Under an argon stream, 5.5 g of (3-(3-iodo-4-hydroxyphenyl)propanoic acid-tyrosine ethyl ester), 5.07 g of 4-dimethylaminopyridine (DMAP), and 50 ml of methylene chloride may be transferred to a 250 ml flask equipped with a funnel. A solution of 3.07 g of ethyl phosphodichloridate (EOP) in 30 ml of methylene chloride may be added to the funnel. The solution in the flask may be cooled down to −40° C. with stirring, and the EOP solution may be added dropwise through the funnel. When the addition is complete, the mixture may be gradually brought up to a temperature of 45° C. and may be maintained at reflux temperature overnight.

The solvent may then be evaporated, and a vacuum (0.1 mm Hg) may be applied for one hour while the temperature of the residue is maintained at 120° C. The residue may be re-dissolved in 100 ml of chloroform, washed with a 0.1M solution of HCl in distilled water, dried over anhydrous $Na_2SO_4$, and quenched into 500 ml of ether. The resulting precipitate may be collected and dried under vacuum.

EXAMPLE 5

Poly(3-(3-iodo-4-hydroxyphenyl)-2-propenoic Acid-tyrosine Ethyl Ester) by Polymerization with EOP Under an argon stream, 5.5 g of (3-(3-iodo-4-hydroxyphenyl)-2-propenoic acid-tyrosine ethyl ester), 5.07 g of 4-dimethylaminopyridine (DMAP), and 50 ml of methylene chloride may be transferred to a 250 ml flask equipped with a funnel. A solution of 3.07 g of ethyl phosphodichloridate (EOP) in 30 ml of methylene chloride may be added to the funnel. The solution in the flask may be cooled down to −40° C. with stirring, and the EOP solution may be added dropwise through the funnel. When the addition is complete, the mixture may be gradually brought up to a temperature of 45° C. and may be maintained at reflux temperature overnight.

The solvent may then be evaporated, and a vacuum (0.1 mm Hg) may be applied for one hour while the temperature of the residue is maintained at 120° C. The residue may be re-dissolved in 100 ml of chloroform, washed with a 0.1M solution of HCl in distilled water, dried over anhydrous $Na_2SO_4$, and quenched into 500 ml of ether. The resulting precipitate may be collected and dried under vacuum.

EXAMPLE 6

Poly(2-(3-iodo-4-hydroxybenzyl)methyl Malonate-tyrosine Ethyl Ester) by Polymerization with EOP Under an argon stream, 7.8 g of (2-(3-iodo-4-hydroxybenzyl-)methyl malonate-tyrosine ethyl ester), 5.07 g of 4-dimethylaminopyridine (DMAP), and 50 ml of methylene chloride may be transferred to a 250 ml flask equipped with a funnel. A solution of 3.07 g of ethyl phosphodichloridate (EOP) in 30 ml of methylene chloride may be added to the funnel. The solution in the flask may be cooled down to −40° C. with stirring, and the EOP solution may be added dropwise through the funnel. When the addition is complete, the mixture may be gradually brought up to a temperature of 45° C. and may be maintained at reflux temperature overnight.

The solvent may then be evaporated, and a vacuum (0.1 mm Hg) may be applied for one hour while the temperature of the residue is maintained at 120° C. The residue may be re-dissolved in 100 ml of chloroform, washed with a 0.1M solution of HCl in distilled water, dried over anhydrous $Na_2SO_4$, and quenched into 500 ml of ether. The resulting precipitate may be collected and dried under vacuum.

EXAMPLE 7

Poly3-(3-iodo-4-hydroxyphenyl)propanoic Acid-tyrosine Ethyl Ester) by Solution Polymerization with CNBR

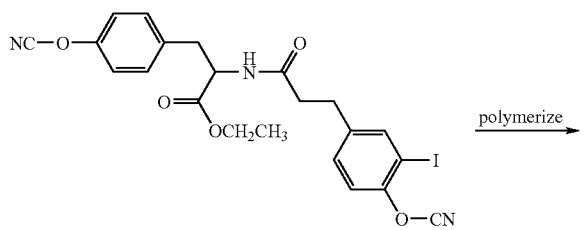

A three-necked, 500 ml round bottom flask equipped with thermometer, overhead stirrer and dropping funnel may be charged with a solution of 21.4 g cyanogen bromide dissolved in 100 ml acetone. The system may be protected from moisture by a CaCl$_2$ drying tube and cooled to −10° C. by means of an external acetone-dry ice cooling mixture. 71 g of (3-(3-iodo-4-hydroxyphenyl)propanoic acid-tyrosine ethyl ester) and 20.2 g of triethylamine may be dissolved in 150 ml acetone and placed in the dropping funnel. With vigorous stirring, the (3-(3-iodo-4-hydroxyphenyl)propanoic acid-tyrosine ethyl ester)/triethylamine solution may be added to the cyanogen bromide solution over a period of 20 minutes. Temperature may be kept below −5° C. Stirring may be continued for an additional 40 minutes; then the reaction mixture may be allowed to warm to +10° C. After completion of the reaction, the dense precipitate of triethylamine hydrobromide may be removed by Buchner filtration. To the clear, colorless filtrate, 500 ml of ice cold water may be added slowly and with stirring over the course of 5 minutes. A dense, crystalline precipitate of (3-(3-iodo-4-hydroxyphenyl)propanoic acid-tyrosine ethyl ester) dicyanate may form, which may be collected on a Buchner funnel, washed with ice cold water, rapidly dried over phosphorous pentoxide in vacuo. The crude material may be recrystallized from hexane

Polymerization of (3-(3-iodo-4-hydroxyphenyl)propanoic acid-tyrosine ethyl ester) dicyanate A 44% (w/v) THF solution of an exactly stoichiometric mixture of (3-(3-iodo-4-hydroxyphenyl)propanoic acid-tyrosine ethyl ester) and (3-(3-iodo-4-hydroxyphenyl)propanoic acid-tyrosine ethyl ester)-dicyanate may be prepared, followed by the addition of 1M potassium tert-butoxide sufficient to yield a solution concentration of 1.0 mole percent. The mixture may be stirred at 23° C. and conversion of dicyanate is monitored spectrophotometrically. Crude product may be obtained by evaporating the solvent. The product may be carefully washed with excess acetone and dried in vacuo.

The foregoing description of the preferred embodiment should be taken as illustrating, rather than as limiting, the present invention as defined by the claims. As would be readily appreciated, numerous variations and combinations of the features set forth above may be utilized without departing from the present invention as set forth in the claims. Such variations are not regarded as a departure from the spirit and scope of the invention, and all such variations are intended to be included within the scope of the following claims.

What is claimed is:

1. An inherently radiopaque, biocompatible, bioresorbable polymer, wherein said polymer comprises one or more recurring units of the Formula (I):

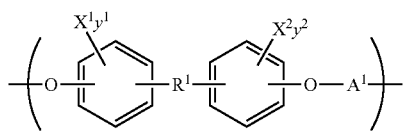

wherein:

$X^1$ and $X^2$ are each independently selected from the group consisting of Br and I;

y1 and y2 are each independently zero or an integer in the range of 1 to 4, with the proviso that the sum of y1 and y2 is at least 1;

$R^1$ is

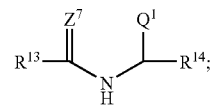

$R^{13}$ and $R^{14}$ are each independently selected from the group consisting of —CH=CH—, —(CH$_2$)$_c$—, —(CHJ$^1$)—, —CHJ$^2$—CHJ$^3$—, —CH=CH—(CHJ$^1$)—, and (CH$_2$)$_c$—(CHJ$^1$)—;

c is zero or an integer in the range of 1 to 8;

$J^1$, $J^2$, and $J^3$ are each independently selected from the group consisting of H, Br, I, —NH—$Q^2$ and —C(=$Z^8$)—O$Q^3$;

$Q^1$, $Q^2$ and $Q^3$ are each independently H or a non-crystallizable group comprising from about 1 to about 30 carbons;

$Z^7$ and $Z^8$ are each independetly O or S;

$A^1$ is selected from the group consisting of

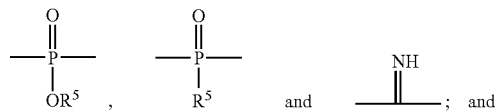

$R^5$ is selected from the group consisting of H, $C_1$-$C_{30}$ alkyl, and $C_1$-$C_{30}$ heteroalkyl.

2. A medical device comprising the polymer of claim 1.

3. The medical device of claim 2, wherein said medical device is configured for placement in a region selected from vascular, musculoskeletal/orthopedic, nervous, respiratory, reproductive, urinary, digestive, endocrine, hematopoietic, or integumentary system.

4. The medical device of claim 2, wherein said medical device is configured for use in vivo.

5. The medical device of claim 2, wherein said medical device is configured for use ex vivo.

6. The medical device of claim 5, wherein said medical device is configured for use in vitro.

7. The medical device of claim 2, wherein said medical device comprises a stent.

8. The medical device of claim 7, wherein said stent further comprises a configuration selected from the group consisting of a sheet stent, a braided stent, a self-expanding stent, a wire stent, a deformable stent, and a slide-and-lock stent.

9. The medical device of claim 7, wherein said stent comprises at least two substantially non-deforming elements arranged to form a tubular member, the non-deforming elements being slidably interconnected for allowing the tubular member to expand from a collapsed diameter to an expanded diameter.

10. The medical device of claim 7, wherein said stent further comprises a tubular member comprising a series of slideably-engaged radial elements and a locking mechanism adapted to permit one-way sliding of the radial elements, such that said tubular member is configured to expand from a first collapsed diameter to a second expanded diameter with minimum recoil.

11. The medical device of claim 2, further comprising an effective amount of a therapeutic agent.

12. The medical device of claim 11, wherein said therapeutic agent is selected from the group consisting of antiproliferative agent, anti-inflammatory agent, anti-matrix metalloproteinase agent, lipid lowering agent, cholesterol modifying agent, anti-thrombotic agent, and antiplatelet agent.

13. The medical device of claim 11, wherein said effective amount is sufficient to provide an effect selected from the group consisting of inhibition of restenosis, inhibition of thrombosis, inhibition of plaque formation, inhibition of plaque rupture, inhibition of inflammation, lowering of cholesterol, and promote healing.

14. The medical device of claim 2, wherein $X^1$ and $X^2$ are iodine.

15. The medical device of claim 2 further comprising a non- halogenated coating.

16. The medical device of claim 2, wherein said polymer forms a coating on at least a portion of said medical device.

17. A system for treating a site within a vessel, comprising the stent of claim 7 and a catheter having a deployment means, wherein said catheter is adapted to deliver the stent to said site and said deployment means is adapted to deploy the stent.

18. A method for re-treatment of a body lumen, comprising:
deploying a first stent along a region within a blood vessel, wherein said first stent is the stent of claim 7, and wherein said first stent resides for a period of time; and
deploying at a later time a second stent, along the approximate same region within the blood vessel, such that the blood vessel is re-treated.

19. The polymer of claim 1, further comprising one or more recurring units of the Formula (II):

wherein:
B is —O—(CHR$^6$)$_p$—O)$_q$-;
R$^6$ is H or C$_1$ to C$_3$ alkyl;
p and q are each individually an integer in the range of about 1 to about 100;
A$^2$ is selected from the group consisting of

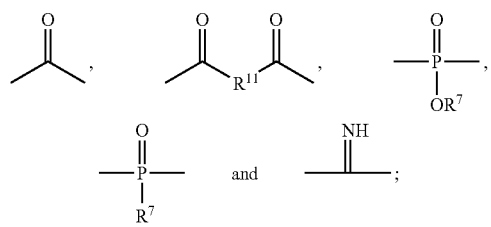

R$^7$ H or a C$_1$ to C$_{30}$ hydrocarbon; and
R$^{11}$ is selected from the group consisting of C$_1$ -C$_{30}$ alkyl, C$_1$ -C$_{30}$ heteroalkyl, C$_5$ -C$_{30}$ aryl, C$_6$ -C$_{30}$ alkylaryl, and C$_2$ -C$_{30}$ heteroaryl.

20. A medical device comprising the polymer of claim 19.

21. The polymer of claim 19, further comprising one or more recurring units of the Formula (Ia):

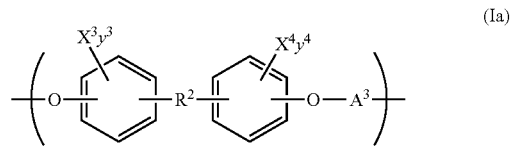

wherein:
X$^3$ and X$^4$ are each independently selected from the group consisting of Br and I;
y3 and y4 are each independently zero or an integer in the range of 1 to 4;
R$^2$ is selected from the group consisting of:

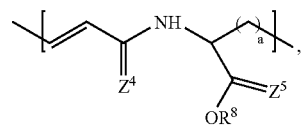

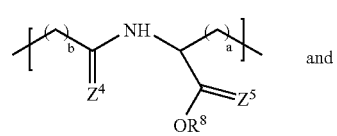

and

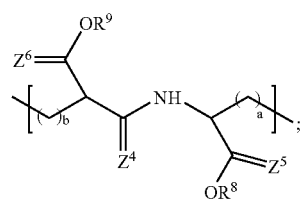

R$^8$ and R$^9$ are each independently H or a non-crystallizable C$_1$ to C$_{30}$ hydrocarbon;
Z$^4$, Z$^5$ and Z$^6$ are each independently O or S;
a and b are each independently an integer in the range of 1 to 8;
A$^3$ is selected from the group consisting of

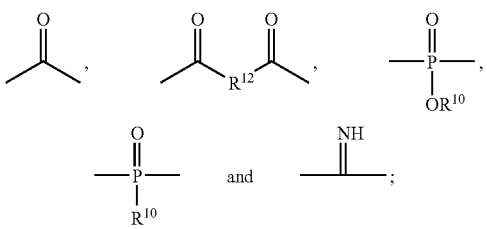

R$^{10}$ is selected from the group consisting of H, C$_1$ -C$_{30}$ alkyl, and C$_1$ C$_{30}$ heteroalkyl; and p1 R$^{12}$ is selected from the group consisting of C$_1$ -C$_{30}$ alkyl, C$_1$ -C$_{30}$ heteroalkyl, C$_5$ -C$_{30}$ aryl, C$_6$ -C$_{30}$ alkylaryl, and C$_2$ -C$_{30}$ heteroaryl.

22. A medical device comprising the polymer of claim 21.
23. The polymer of claim 1, wherein $R^1$ is:

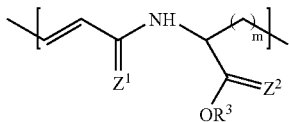

wherein $R^3$ is H or a non-crystallizable $C_1$ to $C_{29}$ hydrocarbon;
$Z^1$ and $Z^2$ are each independently O or S; and
m is an integer in the range of 1 to 8.
24. A medical device comprising the polymer of claim 23.
25. The polymer of claim 1, wherein $R^1$ is:

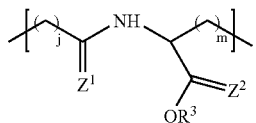

wherein $R^3$ is H or a non-crystallizable $C_1$ to $C_{29}$ hydrocarbon;
$Z^1$ and $Z^2$ are each independently O or S; and
j and m are each independently an integer in the range of 1 to 8.
26. A medical device comprising the polymer of claim 25.
27. The polymer of claim 1, wherein $R^1$ is:

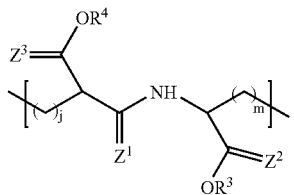

wherein $R^3$ and $R^4$ are each independently H or a non-crystallizable $C_1$ to $C_{29}$ hydrocarbon;
$Z^1$, $Z^2$ and $Z^3$ are each independently O or S; and
j and m are each independently an integer in the range of 1 to 8.
28. A medical device comprising the polymer of claim 27.
29. The medical device of claim 2, further comprising an effective amount of a radiopacifying agent.
30. The medical device of claim 2, further comprising an effective amount of a magnetic resonance enhancing agent.

* * * * *